United States Patent [19]

Miller et al.

[11] Patent Number: 4,503,155
[45] Date of Patent: Mar. 5, 1985

[54] MULTIFUNCTIONAL, CLONING VECTORS FOR USE IN STREPTOMYCES, BACILLUS, AND E. COLI

[75] Inventors: James R. Miller; Jeffrey T. Fayerman; Steven Kovacevic; Nancy E. Beerman, all of Indianapolis, Ind.

[73] Assignee: Eli Lilly and Company, Indianapolis, Ind.

[21] Appl. No.: 344,710

[22] Filed: Feb. 1, 1982

[51] Int. Cl.³ .................. C12N 15/00; C12N 1/20; C12N 1/00
[52] U.S. Cl. .................. 435/172.3; 435/253; 435/317; 435/832; 435/886; 435/849
[58] Field of Search ............ 435/172, 253, 317, 832, 435/886, 849

[56] References Cited

U.S. PATENT DOCUMENTS 4,340,674  7/1982  Manis et al. ................... 435/172

OTHER PUBLICATIONS

Thomas et al., Regions of Broad–Host Range Plasmid RK2 which are Essential for Replication and Maintenance, J. of Bact., 1980, vol. 141, pp. 213–222.
Kreft et al., Recombinant plasmids capable of replication in B. subtilis and E. coli, in Chem. Absts., vol. 89, 1978, p. 411, 103524r.
deVos, et al., 1981, Molecular and General Genetics, 181:424–433.
Dean and Dooley, 1981, in NIH Publication No. 82–99, Recombinant DNA Technical Bulletin, 4(4):143–151.
Nord, 1966, Advances in Enzymology, vol. 28, Interscience Publishers, New York, New York, pp. 238–244.
Ogawara, 1975, Antimicrobial Agents and Chemotherapy, 8(4):402–408.
Bertani, 1951, Journal of Bacteriology, 62:292–300.
Gryczan, J. et al., J. of Bacteriology, 141(1): 246, 1980.
Toyama, H., Plasmid 5: 306, 1981.
Gray, O. et al., Abstracts of the 80th Annual ASM Meeting, Paper No. H68, 1980.
Ehrlich, S. C., Proc. Nat'l. Acad. Sci., USA, 75(3): 1433, 1978.
Goebel, W. et al., Genetic Engineering, Elsevier/North–Holland Biomedical Press, 335 Jan van Galenstraat, P.O. Box 211, Amsterdam, Netherlands, pp. 47–58, 1978.
Gryczan, J. and Dubnau, D., Proc. Nat'l. Acad. Sci., USA, 75(3): 1428, 1978.

Primary Examiner—David M. Naff
Assistant Examiner—K. S. McCowin
Attorney, Agent, or Firm—Gerald V. Dahling; Arthur R. Whale

[57] ABSTRACT

The present invention discloses multifunctional recombinant DNA cloning vectors for use in Streptomyces, Bacillus, and E. coli. The invention further discloses transformants of the aforementioned vectors.

52 Claims, 15 Drawing Figures

Restriction Site and Functional Map of Plasmid pEL103

Restriction Site and Functional Map
of Plasmid pLR1**

Restriction Site and Functional Map of Plasmid pLR2

Restriction Site and Functional Map of Plasmid pHI-16

Restriction Site and Functional Map of Plasmid pHI-18

Restriction Site and Functional Map of Plasmids pBS 1 and pBS 3 pBS 1 pBS 3

Restriction Site and Functional Map of Plasmids pBS 2 and pBS 4 pBS 2 pBS 4

Restriction Site and Functional Map of Plasmids pEL107 and pEL105 pEL 107 pEL 105

Restriction Site and Functional Map of Plasmids pEL109 and pEL110 pEL 109 pEL 110

Restriction Site and Functional Map
of Plasmids pEL113 and pEL114** pEL 113 pEL 114

Restriction Site and Functional Map of Plasmids pEL115 and pEL116 pEL 115 pEL 116

Restriction Site and Functional Map of Plasmids pEL121 and pEL122 pEL 121 pEL 122

Restriction Site and Functional Map of Plasmids pBS5 and pBS6 pBS 5 pBS 6

Restriction Site and Functional Map
of Plasmids pBS 7 and pBS 8

Restriction Site and Functional Map
of Plasmids pBS 9 and pBS 10**

MULTIFUNCTIONAL, CLONING VECTORS FOR USE IN STREPTOMYCES, BACILLUS, AND E. COLI

The present invention comprises novel multifunctional recombinant DNA cloning vectors comprising a functional Streptomyces origin of replication, a functional Bacillus origin of replication, a functional E. coli origin of replication, and one or more DNA segments that confer resistance to antibiotics. The invention further comprises transformants of the aforementioned vectors.

The present invention provides antibiotic resistance conferring cloning vectors for use in Streptomyces, Bacillus, and E. coli. Heretofore, the development and exploitation of recombinant DNA technology in the above organisms has been retarded and made especially difficult in part because of the general lack of selectable multifunctional cloning vectors. The vectors of the present invention are functional and selectable in Streptomyces, Bacillus, and E. coli and therefore represent a significant advance in the technical art.

The present vectors are particularly useful because they are small, versatile, and can be transformed and selected in Streptomyces, Bacillus, or E. coli cells that are sensitive to an antibiotic for which resistance is conferred. Since over half of the clinically important antibiotics are produced by Streptomyces strains, it is desirable to develop cloning systems and vectors that are applicable to that industrially important group. Moreover, since the vectors of the present invention are also functional in Bacillus and E. coli, the intergeneric transfer and expression of genetic material is facilitated. In this context, the present invention provides for flexibility in the selection of host cells for the production of products by recombinant DNA techniques. This is critically important because genetic expression of vector borne genes is limited and influenced by the cellular genetic background into which the genes are transformed. The present invention exploits these host cell differences by providing vectors that can be used intergenerically. Thus, the present vectors can be used to clone genes for increasing the yields of known antibiotics as well as for producing new antibiotics and antibiotic derivatives in a variety of host cells including especially either or both of Streptomyces and Bacillus.

The present invention not only provides multifunctional vehicles for cloning DNA into Streptomyces, Bacillus, and E. coli host cells, but also allows for the convenient selection of transformants. Since transformation is a very low frequency event, such a functional test is a practical necessity for determining which cell(s), of among the millions of cells, has acquired the plasmid DNA. This is important because DNA sequences that are non-selectable can be inserted onto the vectors and, upon transformation into a host, cells containing the vector and the particular DNA sequence of interest can be isolated by appropriate antibiotic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a stable and heritable change in the recipient cell.

Transformant—a recipient host cell that has undergone transformation.

Multifunctional—denotes intergeneric functionality.

Sensitive Host Cell—a host cell that cannot grow in the presence of a given antibiotic without a DNA segment that confers resistance thereto.

Restriction Fragment—any linear portion or whole of a plasmid generated by the action of one or more restriction enzymes on the plasmid.

Insertional Isomer—one of the two or more possible recombinant DNA molecules formed when a DNA fragment is inserted at one of two or more compatible sites on the recipient DNA.

Plasmid pLR2 1.6 kb BamHI Restriction Fragment—the same 1.6 kb BamHI thiostrepton resistance conferring fragment contained in plasmid pIJ6.

Plasmid pLR1 3.4 kb BamHI Restriction Fragment—the same 3.4 kb BamHI neomycin resistance conferring fragment contained in plasmid pIJ2.

$Amp^R$—the ampicillin resistant phenotype.
$Tet^S$—the tetracycline sensitive phenotype.
$Thio^R$—the thiostrepton resistant phenotype.
$Neo^R$—the neomycin resistant phenotype.
$Cm^R$—the chloramphenicol resistant phenotype.
$Kn^R$—the kanamycin resistant phenotype.

DETAILED DESCRIPTION OF THE INVENTION

The present invention comprises multifunctional recombinant DNA cloning vectors comprising:
(a) two or more functionally different origins of replication that are independently selected from the group consisting of any origin of replication that is functional in Streptomyces, any origin of replication that is functional in Bacillus, and any origin of replication that is functional in E. coli, and
(b) one or more DNA segments that confer resistance to at least one antibiotic when transformed into a sensitive host cell in which an origin of replication comprising said vector is functional, said host cells being susceptible to transformation, cell division, and culture, subject to the limitation that when said vector is limited to two functionally different origins of replication, neither of the origins of replication are functional in E coli.

The invention further comprises transformants of the aforementioned vectors.

Vectors of the present invention are constructed by ligating (1) a restriction fragment comprising both an origin of replication that is functional in Streptomyces and also one or more DNA segments that confer resistance to at least one antibiotic when transformed into Streptomyces, with (2) a restriction fragment comprising both an origin of replication that is functional in Bacillus and also one or more DNA segments that confer resistance to at least one antibiotic when transformed into Bacillus. The resulting multifunctional plasmid is novel and functional in both Streptomyces and Bacillus. Ligation of this plasmid with a replicon containing and antibiotic resistance conferring restriction fragment of an E. coli plasmid results in a multifunctional plasmid that is novel and functional in each of Streptomyces, Bacillus, and E. coli.

A preferred first fragment, exemplified herein for illustrative purposes by the ~4.4 kb BamHI restriction fragment of plasmid pEL105, is constructed by ligating the thiostrepton resistance conferring ~1.6 kb BamHI restriction fragment of plasmid pLR2 onto the ~2.8 kb BamHI restriction fragment of plasmid pEL103. The latter fragment contains an origin of replication that is functional in Streptomyces and thus is especially useful for constructing the present invention. A preferred second fragment is the ~4.6 kb BamHI restriction fragment of plasmid pHI-16. The plasmid pHI-16 fragment contains a Bacillus functional origin of replication and also DNA segments that confer antibiotic resistance in Bacillus. Ligation of the first and second restriction fragments results in the novel illustrative multifunctional plasmid pBS2. Ligation of BamHI restricted plasmid pBS2 with BamHI restricted plasmid pBR322 results in the novel multifunctional illustrative plasmid pBS49. Plasmids of the latter type are highly versatile and can be used in each of Streptomyces, Bacillus, and *E. coli*.

Figure 1:
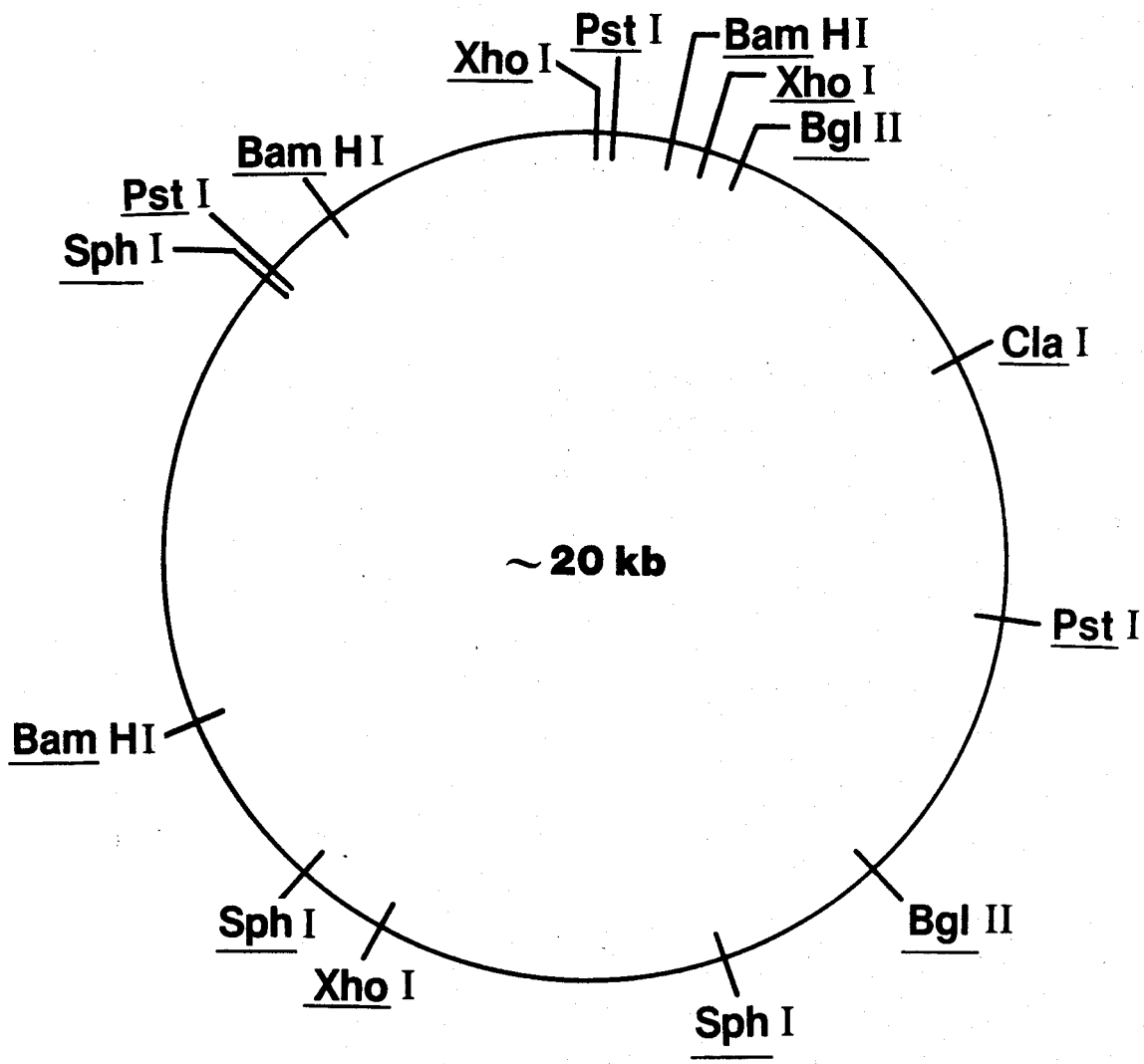

Plasmid pEL103, which contains an origin of replication that is functional in Streptomyces, is approximately 20.0 kb and contains several restriction sites which are particularly advantageous for molecular cloning. Since the origin of replication of plasmid pEL103 has been localized to within the ~2.8 kb BamHI restriction fragment, a variety of different origin of replication containing fragments can be generated by digesting the plasmid with restriction enzymes that cut outside the ~2.8 kb BamHI region. A detailed restriction site and functional map of plasmid pEL103 is presented in FIG. 1 of the accompanying drawings. For purposes of the present application, FIG. 1 and all subsequent figures are not drawn to scale.

Plasmid pEL103 can be conventionally isolated from *Streptomyces granuloruber* No. A39912.13/pEL103, a strain deposited and made part of the permanent stock culture collection of the Northern Regional Research Laboratory, Peoria, Ill. It is available to the public, as a preferred source and stock reservoir of the plasmid, under the accession number NRRL 12549.

Although many different origin of replication containing fragments of plasmid pEL103 can be constructed, the ~2.8 kb BamHI restriction fragment is most preferred for purposes of constructing the present invention. The ~2.8 kb fragment is ligated to one or more antibiotic resistance conferring DNA fragments which are exemplified herein, for illustrative purposes, by the thiostrepton resistance conferring ~1.6 kb BamHI restriction fragment of plasmid pLR2 and the neomycin resistance conferring ~3.4 kb BamHI restriction fragment of plasmid pLR1.

Figure 2:
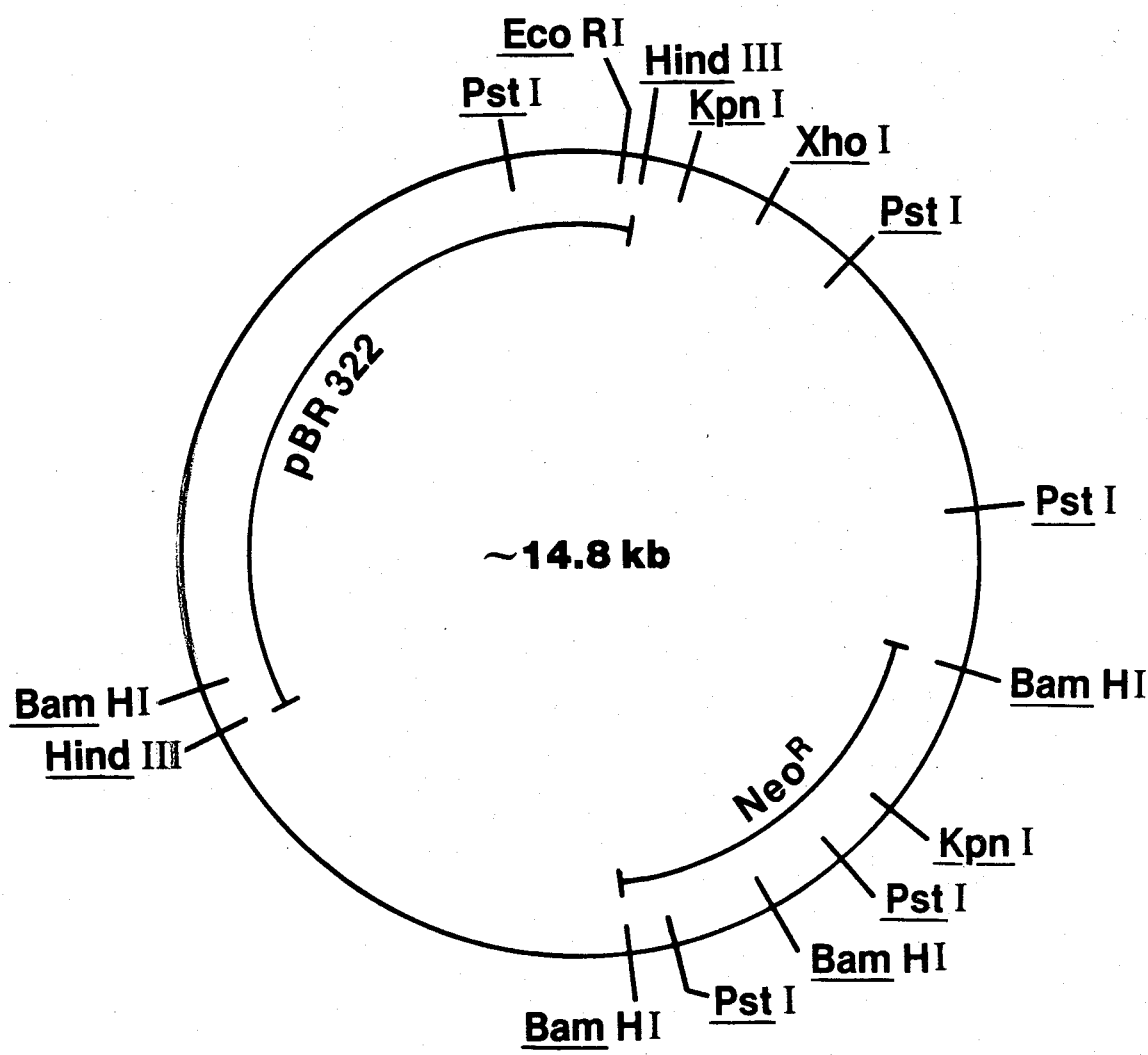
Figure 3:
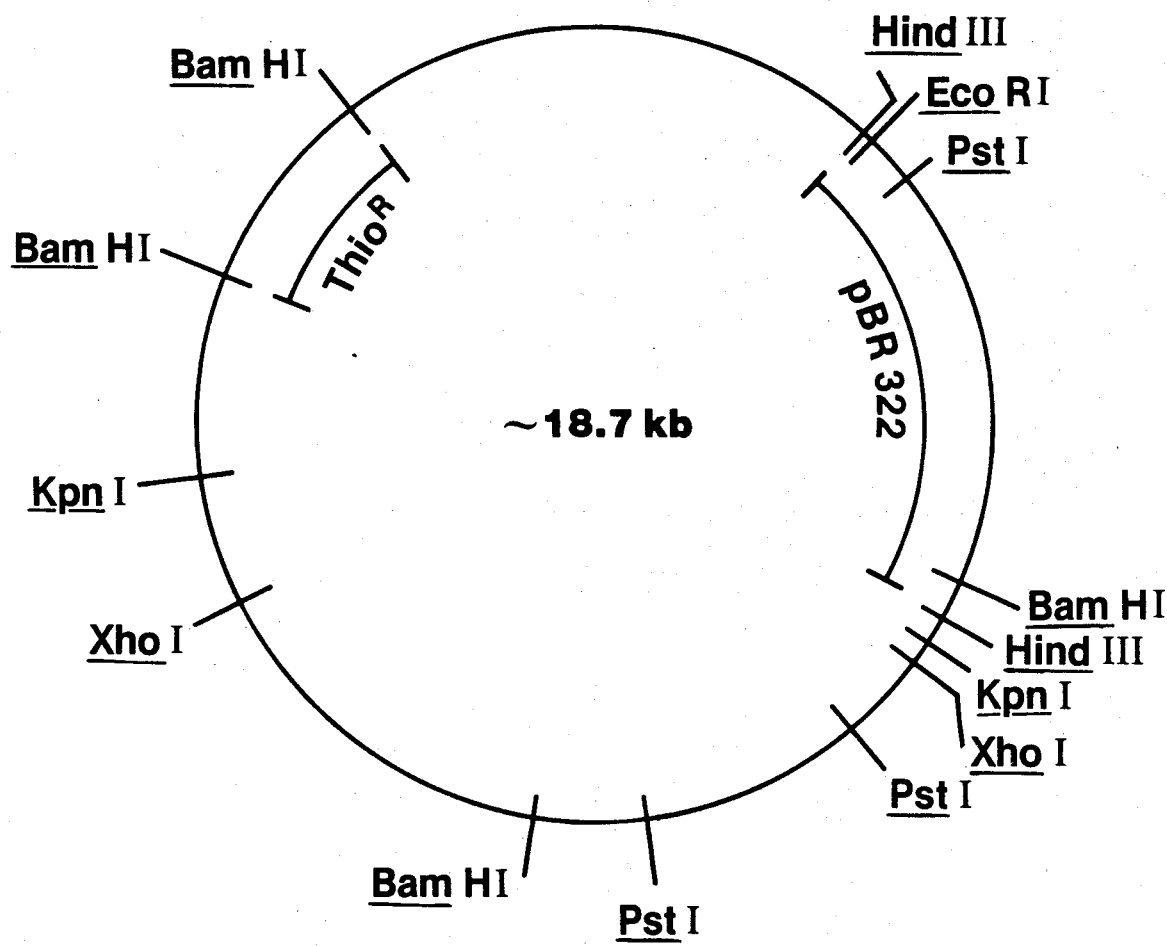

Plasmid pLR2, the source of the thiostrepton resistance conferring fragment, is approximately 18.7 kb and is constructed by ligating HindIII treated plasmid pIJ6, disclosed in Thompson et al., 1980, Nature 286:525, to HindIII treated plasmid pBR322. Plasmid pLR1, the source of the neomycin resistance conferring fragment, is approximately 14.8 kb and is similarly constructed, except that plasmid pIJ2, disclosed in Thompson et al., 1980, is used instead of plasmid pIJ6. Both plasmids pLR2 and pLR1 are functional in *E. coli* and therefore can be amplified and isolated conveniently for subsequent manipulation. A restriction site and functional map of each of plasmids pLR1 and pLR2 is presented respectively in FIGS. 2-3 of the accompanying drawings.

The thiostrepton resistance conferring ~1.6 kb BamHI fragment and the neomycin resistance conferring ~3.4 kb BamHI fragment are ligated to the ~2.8 kb origin of replication containing BamHI fragment of plasmid pEL103 to produce plasmids useful as starting materials for constructing the present invention. The plasmid starting materials are of two orientations depending upon the orientation of the particular resistance conferring DNA fragment. Thus, ligation of the ~1.6 kb BamHI fragment of plasmid pLR2 onto the ~2.8 kb BamHI fragment of plasmid pEL103 results in useful starting material plasmids pEL107 and pEL105; ligation of the ~3.4 kb BamHI fragment of plasmid pLR1 results in useful starting material plasmids pEL109 and pEL110; and ligation of both of the fragments results in useful starting material plasmids pEL113, pEL114, pEL115, and pEL116. The aforementioned plasmid starting materials can be partially BamHI digested to generate restriction fragments that are useful for constructing the present vectors as described herein below.

Figure 4:
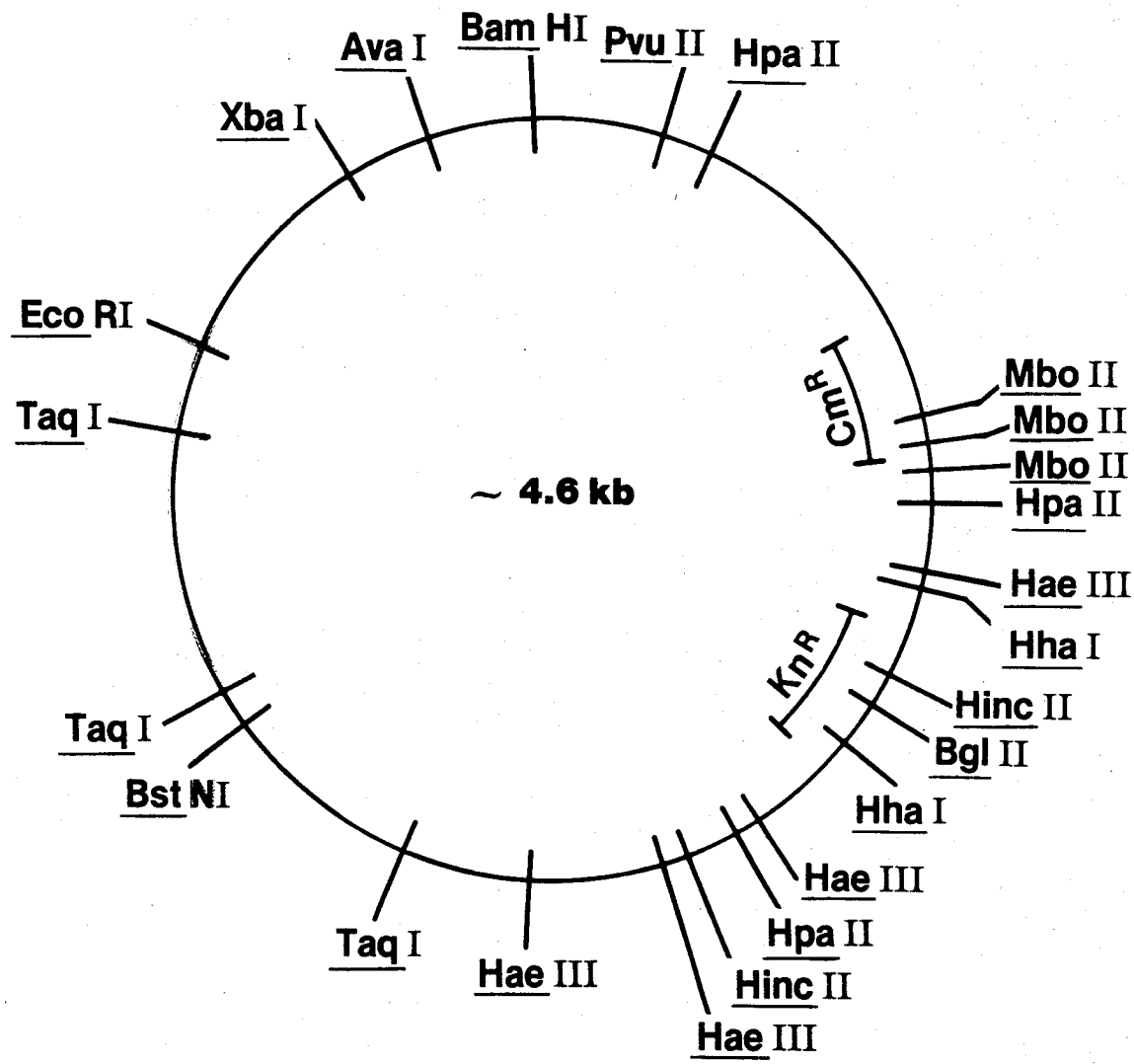

Plasmid pHI-16 contains both an origin of replication that is functional in Bacillus and also DNA segments that respectively confer resistance to antibiotics chloramphenicol and kanamycin. Therefore, plasmid pHI-16 is an excellent starting material for purposes of the present invention. Plasmid pHI-16 is ~4.6 kb and results from an in vivo deletion of known chimeric plasmid pBD12 (disclosed in Gryczan et al., 1980, J. Bacteriology 141 (1):246) and can be conventionally isolated from *Bacillus subtilis* MI112/pHI-16, a constructed strain deposited and made part of the permanent stock culture collection of the Northern Regional Research Laboratory, Peoria, Ill. It is available to the public, as a preferred source and stock reservoir of the plasmid, under the accession number NRRL B-12597. A detailed restriction site and functional map of plasmid pHI-16 is presented in FIG. 4 of the accompanying drawings. For simplicity, only three MboII and TaqI restriction sites are shown for plasmid pHI-16 and the pHI-16 fragments illustrated herein.

Figure 5:
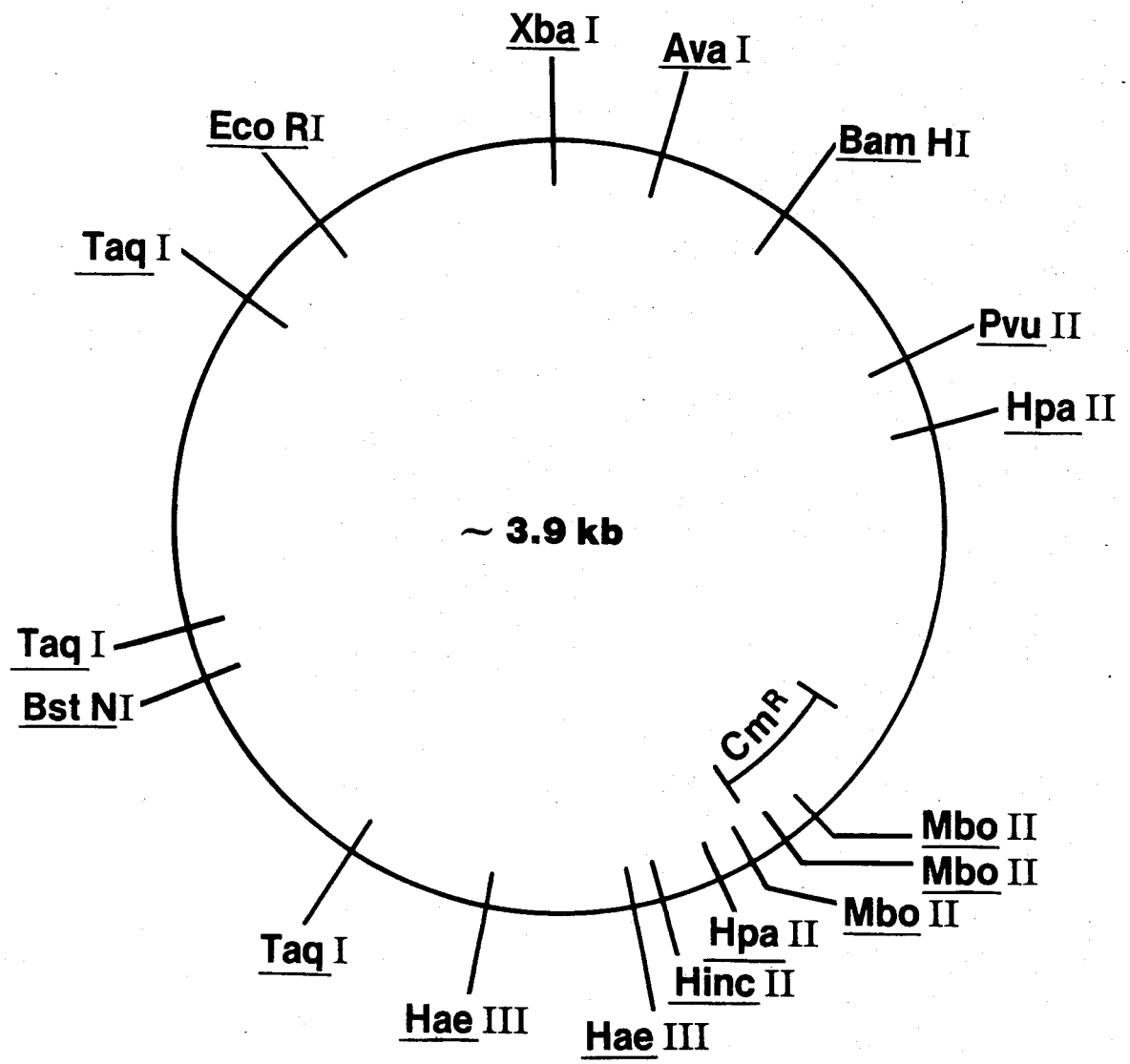
Figure 6:
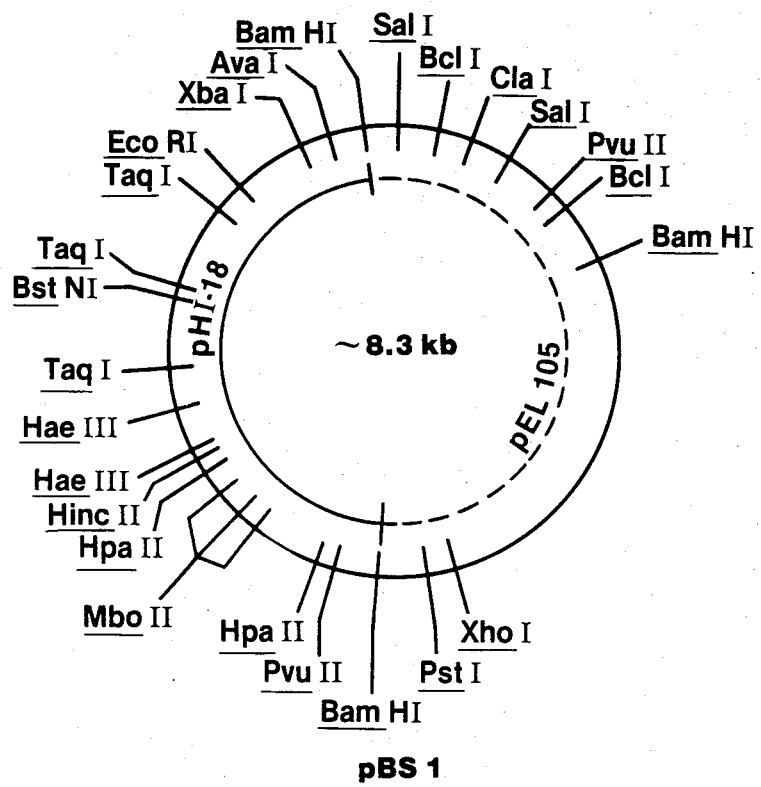
Figure 6:
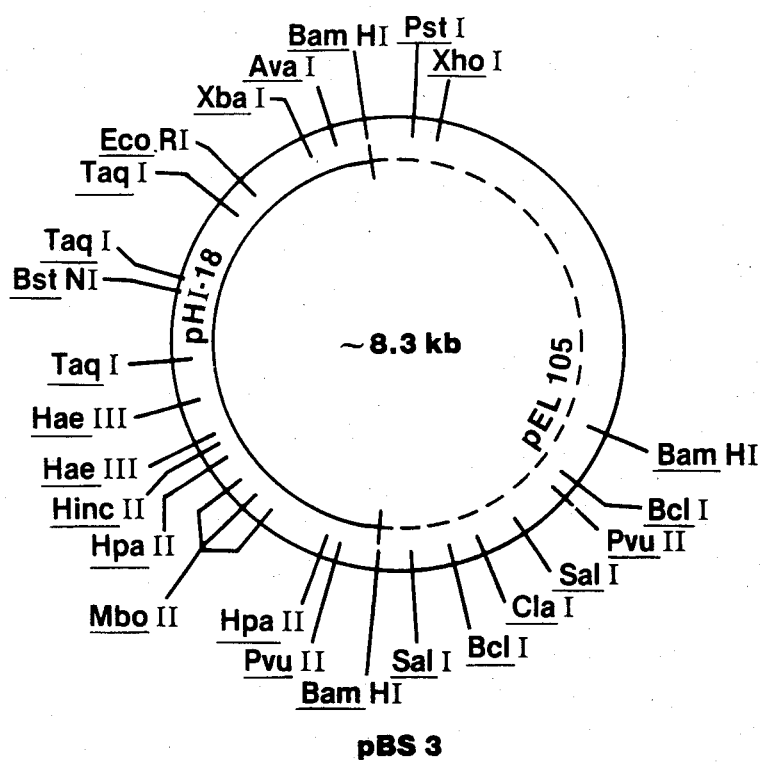
Figure 7:
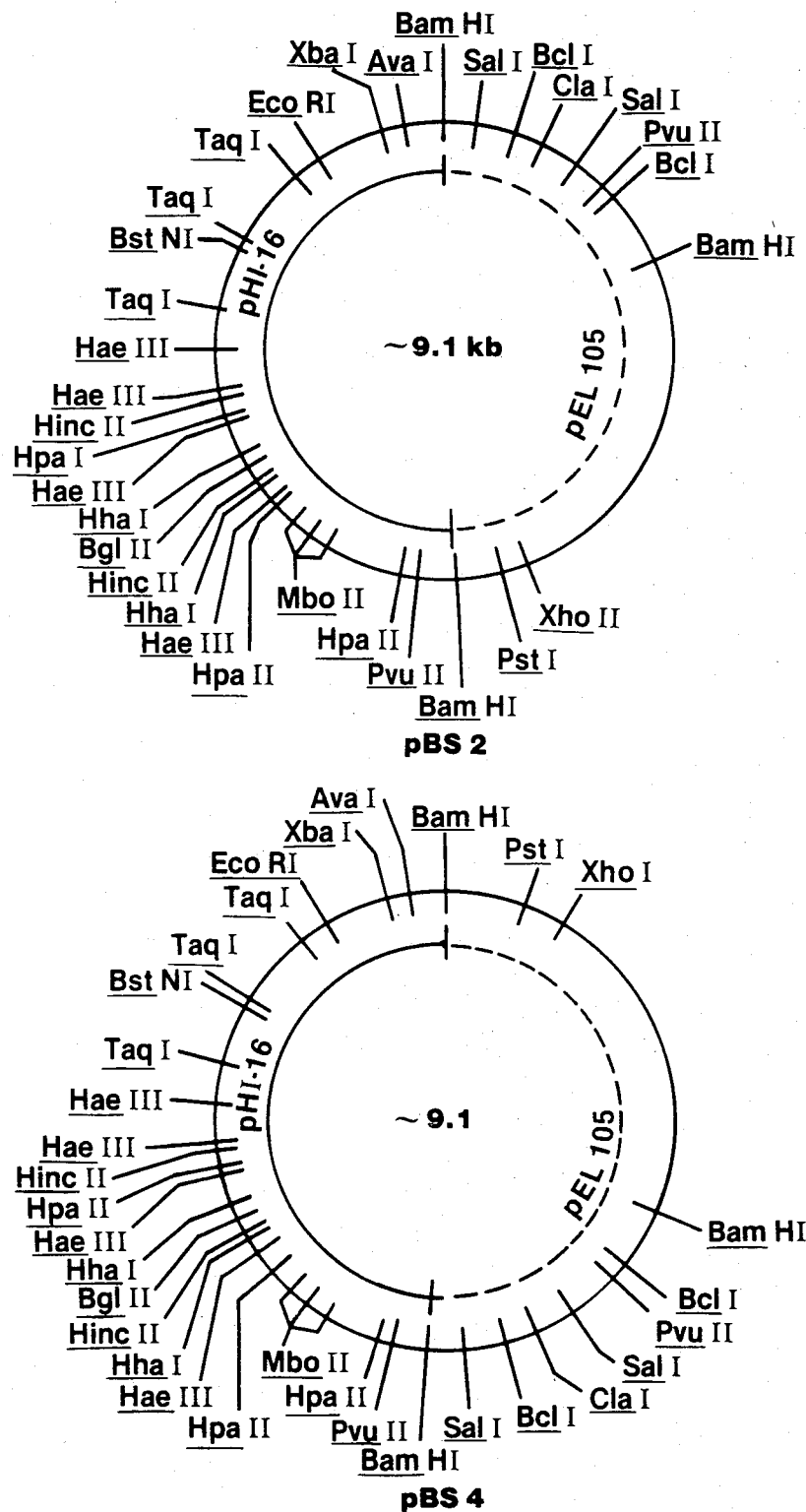

Various derivatives of plasmid pHI-16 can also be used as starting materials. For example, deletion of the ~0.7 kb HpaII restriction fragment of plasmid pHI-16 results in the novel plasmid pHI-18. Plasmid pHI-18 is ~3.9 kb and contains a chloramphenicol resistance conferring DNA segment as well as an origin of replication that is functional in Bacillus. A restriction site and functional map of plasmid pHI-18 is presented in FIG. 5 of the accompanying drawings. For simplicity, only three MboII and TaqI restriction sites are shown for plasmid pHI-18 and the pHI-18 fragments illustrated herein.

The BamHI digestion of plasmids pHI-16 and pHI-18 results respectively in ~4.6 kb and ~3.9 kb fragments which, with respect to Bacillus, each contain an origin of replication and also DNA conferring antibiotic resistance. Therefore, multifunctional cloning vectors, illustrative of the present invention, can be readily constructed by ligating the ~3.9 kb BamHI restriction fragment of plasmid pHI-18 or the ~4.6 kb BamHI restriction fragment of plasmid pHI-16 with the ~4.4 kb BamHI restriction fragment of plasmid pEL105 disclosed above. The resulting multifunctional plasmids are herein respectively designated as plasmids pBS1 and pBS2. Ligation of the ~4.6 kb BamHI restriction fragment of plasmid pHI-16 with the ~6.2 kb BamHI restriction fragment of plasmid pEL110 results in the novel multifunctional plasmid pBS5. Similarly, ligation of the plasmid pHI-16 BamHI fragment with the ~7.8 kb BamHI restriction fragment of plasmid pEL113 results in the multifunctional plasmid pBS7. A detailed restriction site and functional map of each of plasmids pBS1, pBS2, pBS5, and pBS7 are presented respectively in FIGS. 6, 7, 13, and 14 of the accompanying drawings.

The present vectors such as, for example, plasmid pBS1, pBS2, pBS5 and pBS7, can be ligated to a functional replicon containing and antibiotic resistance conferring restriction fragment of an E. coli plasmid such as, for example, plasmid pBR322, pBR324 (disclosed in Bolivar, F., 1978, Gene 4:121), pBR325 (disclosed in Bolivar, F., 1978, Gene 9:287), or the like, to produce novel multifunctional plasmids for use in E. coli, Streptomyces, and Bacillus. These constructions, exemplified for illustrative purposes by plasmids pBS9 and pBS10, are particularly advantageous because amplification and manipulation of plasmids can be done faster and more conveniently in E. coli than in either Streptomyces or Bacillus. Thus, after desired recombinant DNA procedures are accomplished within the E. coli host system, the particular DNA can be removed, reconstructed to plasmid form (if necessary), and then transformed into a Streptomyces or Bacillus host cell.

Although the Streptomyces functional origin of replication that is exemplified in the present multifunctional pBS plasmids is contained in the ~2.8 kb BamHI fragment of plasmid pEL103, analogous pEL103 fragments can also be used provided that the origin of replication is present. Such analogous plasmid pEL103 restriction fragments include, but are not limited to, the PstI, SphI, BglII, ClaI, XhoI, and the other BamHI fragments. Moreover, a particular antibiotic resistance conferring DNA segment is not limited to a single position on a plasmid pEL103 restriction fragment but can be ligated or inserted at varying sites provided that the origin of replication or other critical plasmid controlled physiological functions are not disrupted. Therefore, many different plasmid pEL103 restriction fragments and derivatives can be used in place of those exemplified herein. Those skilled in the art understand or can readily determine which sites are advantageous for the ligation or insertion of a particular DNA segment.

While the ~4.6 and 3.9 kb BamHI restriction fragments of plasmids pHI-16 and pHI-18 respectively are preferred for constructing the present multifunctional plasmids, many different origin of replication containing and antibiotic resistance conferring fragments of plasmids pHI-16 and pHI-18 can also be used. Analogous single cut restriction fragments of plasmids pHI-16 and pHI-18 include, for example, the BglII, XbaI, EcoRI, PvuII, and AvaI fragments of plasmid pHI-16 and the XbaI, EcoRI, PvuII, and AvaI fragments of plasmid pHI-18. In addition, the antibiotic resistance conferring DNA segments, contained in the plasmid pHI-16 and pHI-18 fragments, are not limited to a single position. Rather, the segments can be positioned and inserted and ligated at varying sites provided that the origin of replication or other critical plasmid controlled physiological functions are not disrupted. Those skilled in the art understand or can readily determine which sites are advantageous for the ligation or insertion of a particular DNA segment. Therefore, a large number of restriction fragments can be constructed that both express antibiotic resistance and also contain an origin of replication that is functional in Bacillus. Such fragments can be used in place of those exemplified herein for constructing additional multifunctional vectors that are also within the scope of the present invention.

Antibiotic resistance conferring DNA segments can also be ligated onto other Bacillus functional plasmids such as, for example, plasmid pBD15 and plasmids (disclosed in NIH Publication No. 82-99, 1981, Recombinant DNA Technical Bulletin 4(4):143) pPL10, pPL7065, pIM13, pPL576, pBC16, pAM77, pC194, pC221, pC223, pE194, pSA2100, pSA0501, TP2, pUB110, pUB112, pBD6, pBD8, pBD9, pBD10, pBD11, pBD12, pBD20, pBD35, pBD64, pOG1196, pHV12, pHV14, pHV33, pOG2165, and pGrTI. The resulting plasmids confer antibiotic resistance, contain an origin of replication that is functional in Bacillus, and thus can be used in place of plasmids pHI-16 and pHI-18 for purposes of the present invention. Therefore, the present invention is not limited to the illustrative multifunctional vectors that require plasmids pHI-16 or pHI-18 for construction.

Although the thiostrepton, neomycin, kanamycin, and chloramphenicol antibiotic resistance conferring DNA segments are, for illustrative purposes, respectively exemplified by the ~1.6 kb BamHI restriction fragment of plasmid pLR2, the ~3.4 kb BamHI restriction fragment of plasmid pLR1, the ~4.6 BamHI restriction fragment of plasmid pHI-16, and the ~3.9 BamHI restriction fragment of plasmid pHI-18, those skilled in the art can construct and substitute either individually or in combination, other DNA segments that also confer resistance to the aforementioned antibiotics. Other thiostrepton resistance conferring DNA segments of plasmid pLR2 include, for example, the ~13 kb PstI restriction fragment and also the BclI subfragment of the ~1.6 kb BamHI restriction fragment. Other neomycin resistance conferring DNA segments of plasmid pLR1 include, for example, the ~3.5 kb PstI restriction fragment and also the larger of the SstI-KpnI subfragments of the ~3.4 kb BamHI restriction fragment. Other kanamycin resistance conferring DNA segments of plasmid pHI-16 include, for example, the ~0.74 kb HpaII fragment and also the larger of the XbaI-PvuII, AvaI-EcoRI, EcoRI-PvuII, and BamHI-EcoRI fragments. Other chloramphenicol resistance conferring DNA segments of plasmid pHI-18 include, for example, the ~0.84 kb HpaII fragment and also the larger of the EcoRI-PvuII, BamHI-EcoRI, and XbaI-PvuII fragments.

Additional DNA segments conferring resistance to the above or to different antibiotics such as, for example, hygromycin, bacteriocin, viamycin, streptomycin, tylosin, and erythromycin, can also be used for purposes of the present invention. Moreover, various functional derivatives of the above described antibiotic resistance conferring DNA segments can be constructed by adding, eliminating, or substituting nucleotides in accordance with the genetic code. Those skilled in the art will understand that ligation of these, or any of the other antibiotic resistance conferring DNA segments, with Streptomyces and Bacillus origins of replication containing restriction fragment, results in multifunctional vectors that are within the scope of the present invention.

The above described origin of replication containing restriction fragments and also the antibiotic resistance conferring DNA segments can be conveniently modified to facilitate subsequent ligation. For example, addition of molecular linkers provides for the construction of specific restriction sites that are useful for ligation or for other purposes known in the art. Moreover, the various restriction fragments can also be modified by adding, eliminating, or substituting nucleotides to alter characteristics and to provide a variety of unique or additional restriction sites. Those skilled in the art understand nucleotide chemistry and the genetic code and thus which nucleotides are interchangeable and which DNA modifications are desirable for a specific purpose.

The recombinant DNA cloning vectors of the present invention are not limited for use in a single species or strain of either Streptomyces or Bacillus. To the contrary, the vectors are broadly applicable and can be transformed into host cells of many Bacillus and Streptomyces taxa, particularly the restrictionless strains thereof. Moreover, with respect to Streptomyces, many of the strains are economically important and produce antibiotics such as aminoglycoside, macrolide, β-lactam, polyether, and glycopeptide antibiotics. Restrictionless strains are readily selected and isolated from Streptomyces and Bacillus taxa by conventional procedures and extensions of principles well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restrictionless.

Preferred host cells of restrictionless strains of Streptomyces taxa that produce aminoglycoside antibiotics and in which the present vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var. *sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and can be transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present vectors are especially useful and can be transformed, include restrictionless cells of, for example: *S. coelicolor, S. granuloruber, S. roseosporus, S. lividans, S. espinosus,* and *S. azureus.*

Preferred host cells of restrictionless strains of Bacillus in which the present vectors are especially useful and can be transformed, include restrictionless cells of, for example, *B. subtilis, B. subtilis* M1112, *B. thuringiensis, B. thuringiensis* var. *israeliensis, B. cereus, B. anthracis, B. piliformis, B. tropicus, B. alvei, B. megaterium, B. pumilus, B. licheniformis, B. polymyxa, B. macerans, B. circulans, B. stearothermophilus, B. coagulans, B. firmus, B. brevis, B. sphaericus, B. pasteurii, B. fastidiosus, B. larvae, B. lentimorbus, B. apiarus, B. amyloliquifaciens, B. laterosporus,* and *B. popillae.*

In addition to the representative Streptomyces and Bacillus host cells described above, the present vectors are also useful and can be transformed into cells of restrictionless strains of other taxa such as, for example: Staphylococcus, Staphylococcus aureus, Streptococcus, related Actinomycetes, including Streptosporangium, Actinoplanes, Nocardia, and Micromonospora, and Lactobacillus. Furthermore, the multifunctional vectors that contain an *E. coli* replicon can also be transformed into *E. coli.* Thus, the vectors of the present invention have wide application and are useful and can be transformed into host cells of a variety of organisms.

While all the embodiments of the present invention are useful, some of the present recombinant DNA cloning vectors and transformants are more preferred than others. Accordingly, preferred vectors are plasmids pBS1, pBS2, pBS5, pBS7 and pBS9; and preferred transformants are *Streptomyces ambofaciens*/pBS1, *S. ambofaciens*/pBS2, *S. ambofaciens*/pBS5, *S. ambofaciens*/pBS7, *S. ambofaciens*/pBS9, *Bacillus subtilis* M1112/pBS1, *B. subtilis*/M1112/pBS2, *B. subtilis*/M1112/pBS5, *B. subtilis*/M1112/pBS7, *B. subtilis*/M1112/pBS9, and *E. coli* K12 HB101/pBS9.

The recombinant DNA cloning vectors and transformants of the present invention have broad utility and help fill the need for suitable multifunctional cloning vehicles for use in Streptomyces, Bacillus, *E. coli*, and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted onto the present vectors and then transformants containing the nonselectable DNA can be isolated by appropriate antibiotic selection. Such non-selectable DNA segments can be inserted at any site, except within regions necessary for plasmid function and replication, and include, but are not limited to, genes that specify antibiotic modification enzymes and regulatory genes of all types.

More particularly, a non-selectable DNA segment that comprises a gene can be inserted on a plasmid such as for example, illustrative plasmid pBS9, at the central SalI restriction site of the ~1.6 kb BamHI resistance conferring fragment. Such an insertion inactivates the thiostrepton resistance gene and thus allows for the easy identification of Streptomyces transformants containing the recombinant plasmid. This is done by first selecting for neomycin resistance and, secondarily, identifying those neomycin resistant Streptomyces transformants that are not resistant to thiostrepton. In a similar manner, insertion of a DNA segment of interest at, for example, the internal BamHI restriction site of the ~3.4 kb BamHI resistance conferring fragment inactivates the neomycin resistance gene. Thus, Streptomyces transformants carrying this recombinant plasmid also are identified easily by first selecting for thiostrepton resistance and, secondarily, identifying those thiostrepton resistant transformants that are not resistant to neomycin. Therefore, the ability to select for antibiotic resistance in Streptomyces allows for the efficient isolation of the extremely rare cells that contain the particular nonselectable DNA of interest.

In addition, a non-selectable DNA segment that comprises a gene can also be inserted on a plasmid such as for example, illustrative plasmid pBS9, at the BglII restriction site of the kanamycin resistance conferring fragment. Such an insertion inactivates the kanamycin resistance gene and thus allows for the easy identification of Bacillus transformants containing the recombinant plasmid. This is done by first selecting for chloramphenicol resistance and, secondarily, identifying those chloramphenicol resistant Bacillus transformants that are not resistant to kanamycin. In a similar manner, insertion of a DNA segment of interest at, for example, the internal MboII restriction site of the chloramphenicol resistance conferring fragment inactivates the chloramphenicol resistance gene. Thus, Bacillus transformants carrying this recombinant plasmid also are identified easily by first selecting for kanamycin resistance and, secondarily, identifying those kanamycin resistant transformants that are not resistant to chloramphenicol. Therefore, the ability to select for antibiotic resistance in Bacillus also allows for the efficient isolation of the extremely rare cells that contain the particular non-selectable DNA of interest. Similar selections can also be done in *E. coli.*

The functional test for antibiotic resistance, as described herein above, is also used to locate DNA segments that enhance copy number or act as control elements and direct expression of an individual antibiotic resistance gene. Such segments, including but not limited to, promoters, attenuators, repressors, inducers, ribosomal binding sites, and the like, are used to control the expression of other genes in cells of Streptomyces, Bacillus, *E. coli*, and related organisms.

The thiostrepton, neomycin, kanamycin, and chloramphenicol resistance conferring vectors of the present invention are also useful for insuring that linked DNA segments are stably maintained in host cells over many generations. These genes or DNA fragments, covalently linked to the thiostrepton, neomycin, kanamycin, or chloramphenicol resistance conferring fragment and propagated either in Streptomyces, Bacillus, *E. coli*, or in the cells of related organisms, are maintained by exposing the transformants to levels of thiostrepton, neomycin, kanamycin, or chloramphenicol that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest, particularly in Streptomyces, Bacillus, and *E. coli.*

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Apramycin, Tobramycin, Erythromycin, and the like. The present invention also provides selectable vectors that are useful for cloning, characterizing, and reconstructing DNA sequences that code for commercially important proteins such as, for example, human insulin, human proinsulin, glucagon, interferon, human growth hormone, bovine growth hormone, and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, Streptomycin, Cephalosporin, Tylosin, Actaplanin, Narasin, Monensin, Apramycin, Tobramycin, and Erythromycin derivatives, or for enzymes that mediate and increase bioproduction of antibiotics or other products. The capability for inserting and stabilizing such DNA segments thus allows for increasing the yield and availability of antibiotics.

The present multifunctional cloning vectors also allow for the genetic expression in Streptomyces of products now bioproduced in *E. coli* and Bacillus. This is especially advantageous because large scale Streptomyces fermentation is better known and understood than is fermentation of either Bacillus or *E. coli*. In fact, large scale commercial fermentation of *E. coli* is still highly experimental and sometimes difficult. The present invention circumvents this problem by providing the alternative of producing compounds now biosynthesized in *E. coli* such as, for example, human insulin, human proinsulin, glucagon, interferon, human growth hormone, bovine growth hormone, and the like, in Streptomyces. This can be done because the present vectors are highly versatile and can accommodate either or both of DNA sequences which express the aforementioned products or sequences comprising entire product producing *E. coli* plasmids. Thus, the present invention allows for flexibility in the choice of hosts and provides a means for the bioproduction of polypeptides and other products in Streptomyces, Bacillus, and *E. coli*. Those skilled in the art know or can readily determine which host is most advantageous for both producing a particular product and for a given fermentation.

*Streptomyces granuloruber* No. A39912.13/pEL103 and *Bacillus subtilis*/MI112/pHI-16, as respective sources of plasmids pEL103 and pHI-16, can be cultured in a number of ways using any of several different media. Carbohydrate sources which are preferred in a culture medium include, for example, molasses, glucose, dextrin, and glycerol, and nitrogen sources include, for example, soy flour, amino acid mixtures, and peptones. Nutrient inorganic salts are also incorporated and include the customary salts capable of yielding sodium, potassium, ammonia, calcium, phosphate, chloride, sulfate, and like ions. As is necessary for the growth and development of other microorganisms, essential trace elements are also added. Such trace elements are commonly supplied as impurities incidental to the addition of other constituents of the medium.

*Streptomyces granuloruber* No. A39912.13/pEL103 is grown under aerobic culture conditions over a relatively wide pH range of about 5 to 9 at temperatures ranging from about 15° to 40° C. For production of plasmid pEL103 at highest copy number, however, it is desirable to start with a culture medium at a pH of about 7.2 and maintain a culture temperature of about 30° C. Culturing *Streptomyces granuloruber* No. A39912.13- /pEL103, under the aforementioned conditions, results in a reservoir of cells from which plasmid pEL103 is isolated conveniently by techniques well known in the art.

*Bacillus subtilis* MI112/pHI-16 is grown under aerobic culture conditions over a relatively wide pH range of about 5.0 to 8.5 at temperatures ranging from about 25° to 45° C. For production of plasmid pHI-16 at highest copy number, however, it is desirable to start with a culture medium at a pH of about 7 and maintain a culture temperature of about 37° C. Culturing *Bacillus subtilis* MI112/pHI-16, under the aforementioned conditions, results in a reservoir of cells from which plasmid pHI-16 is isolated conveniently by techniques well known in the art.

The following examples further illustrate and detail the invention disclosed herein. Both an explanation of and the actual procedures for constructing the invention are described where appropriate.

EXAMPLE 1

Isolation of Plasmid pEL103

A. Culture of *Streptomyces granuloruber* No. A39912.13/pEL103

A vegetative inoculum of *Streptomyces granuloruber* No. A39912.13/pEL103 (NRRL 12549) was conventionally prepared by growing the strain under submerged aerobic conditions in 50 ml. of sterilized trypticase soy broth* at 35 g./l. in deionized water.

*Trypticase soy broth is obtained from BBL Division, Becton-Dickinson & Company, Cockeysville, Md. 21030.

The trypticase soy broth inoculum was incubated for 48 hours at a temperature of 30° C. After incubation, about 10 ml. of the inoculum was transferred to 500 ml. of the sterilized broth and was incubated for about 20 hours at 30° C. The pH was not adjusted. After incubation, the *Streptomyces granuloruber* No. A39912.13- /pEL103 cells were ready for harvest and subsequent isolation of plasmid DNA.

B. Plasmid Isolation

About 12 g. (wet wgt) of *Streptomyces granuloruber* No. A39912.13/pEL103 cells were centrifuged (10 minutes, 4° C., 10,000 rpm), washed in 10% glycerol, and then harvested by recentrifugation under the aforementioned conditions. About 50 ml. of TES buffer (0.01 M Tris(hydroxymethyl)aminoethane [Tris], 0.001 M EDTA, 34% sucrose, pH 8) were added to the cells followed by about 0.25 g. of lysozyme in 10 ml. of 0.25 M EDTA. After the mixture was incubated at 37° C. for about 15 minutes, about 0.5 ml. of 10% Triton X-100 in TE buffer (0.01 M Tris, 0.001 M EDTA, pH 8) was added. The resultant mixture was then incubated at 65° C. for about 15 minutes. After the lysate was centrifuged (45 minutes, 4° C., 18,000 rpm), the supernatant was extracted four times with isoamyl alcohol and once with a chloroform:isoamyl alcohol solution (24:1). Next, 0.1 volume of 3M sodium acetate was added to the aqueous phase followed by 3 volumes of cold (−20° C.) 95% ethanol. The ethanol precipitation was rapidly performed in a dry ice-ethanol bath and the DNA precipitate was collected by centrifugation (15 minutes, 4° C., 10,000 rpm). The precipitate was vacuum dried and then resuspended in 1.1 ml. of STE buffer (0.01 M Tris, 0.001 M EDTA, 0.01 M sodium chloride). Centrifugation (40 hours, 15° C., 35,000 rpm) using cesium chloride gradients, with ethidium bromide, was carried out to purify the plasmid DNA. Following centrifugation, the desired plasmid pEL103 DNA band was removed and the ethidium bromide extracted by conventional procedures. After precipitation of the DNA in 3 volumes of ethanol, the thus isolated plasmid pEL103 DNA was dissolved in 1 ml. of 10 fold diluted TE buffer and was then stored at −20° C.

EXAMPLE 2

Construction of Plasmid pLR2

A HindIII Digestion of Plasmid pIJ6

About 20 µl. (20 µg.) of plasmid pIJ6 DNA, disclosed in Thompson et al., 1980, Nature 286:525, 5 µl. BSA (Bovine Serum albumin, 1 mg./ml.), 19 µl. water, 1 µl. of HindIII (containing 3 New England Bio Labs units) restriction enzyme*, and 5 µl. reaction mix** were incubated at 37° C. for 2 hours. The reaction was terminated by the addition of about 50 µl. of 4M ammonium acetate and 200 µl. of 95% ethanol. The resultant DNA precipitate was washed twice in 70% ethanol, dried in vacuo, suspended in 20 µl. of TE buffer, and stored at −20° C.

*Restriction enzymes can be obtained from the following sources: New England Bio Labs., Inc., 32 Tozer Road, Beverly, Mass. 01915; Boehringer-Mannheim Biochemicals, 7941 Castleway Drive, Indianapolis, Ind. 46250.
**Reaction mix for HindIII restriction enzyme was prepared with the following composition. 600mM NaCl, 100mM Tris-HCl, pH7.9, 70mM MgCl$_2$, 10mM Dithiothreitol.

B. HindIII Digestion of Plasmid pBR322

About 8 µl. (4 µg.) of plasmid pBR322 DNA*, 5 µl. reaction mix, 5 µl. BSA (1 mg./ml.), 31 µl. water, and 1 µl. of HindIII restriction enzyme were incubated at 37° C. for 2 hours. After the reaction was terminated by incubating at 60° C. for 10 minutes, about 50 µl. of ammonium acetate and 200 µl. of 95% ethanol were added. The resultant DNA precipitate was washed twice in 70% ethanol, dried in vacuo, and suspended in 45 µl. of water.

*Plasmid pBR322 can be obtained from Boehringer-Mannheim Biochemicals the address of which is disclosed in Example 2A.

C. Ligation of HindIII Digested Plasmids pIJ6 and pBR322

About 20 µl. of HindIII treated plasmid pIJ6 (from Example 2A), 20 µl. of HindIII treated plasmid pBR322 (from Example 2B), 5 µl. BSA (1 mg./ml.), 1 µl. of T4 DNA ligase*, and 5 µl. ligation mix** were incubated at 16° C. for 4 hours. The reaction was terminated by the addition of about 50 µl. 4M ammonium acetate and 200 µl. of 95% ethanol. The resultant DNA precipitate was washed twice in 70% ethanol, dried in vacuo, and suspended in TE buffer. The suspended DNA constituted the desired plasmid pLR2.

*T4 DNA ligase can be obtained from the following source: New England Bio Labs., Inc., 32 Tozer Rd., Beverly, Mass. 01915.
**Ligation mix was prepared with the following composition. 500mM Tris-HCl, pH7.8, 200mM Dithiothreitol, 100mM MgCl$_2$, 10mM ATP.

EXAMPLE 3

Construction of E. coli K12 HB101/pLR2

About 10 ml. of frozen competent E. coli K12 HB101 cells (Bolivar et al., 1977, Gene 2:75-93) were pelleted by centrifugation and then suspended in about 10 ml. of 0.01M sodium chloride. Next, the cells were pelleted again, resuspended in about 10 ml. of 0.03M calcium chloride, incubated on ice for 20 minutes, pelleted a third time, and finally, resuspended in 1.25 ml. of 0.03M calcium chloride. The resultant cell suspension was competent for subsequent transformation.

Plasmid pLR2 in TE buffer (prepared in Example 2C) was ethanol precipitated, suspended in 150 µl. of 30mM calcium chloride solution, and gently mixed in a test tube with about 200 µl. of competent E. coli K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 µg./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, New York) containing ampicillin. Surviving colonies were selected and tested for the expected phenotype (Amp$^R$, Tet$^S$), and constituted the desired E. coli K12 HB101/pLR2 transformants.

EXAMPLE 4

Construction of Plasmid pLR1

Plasmid pLR1 was prepared in substantial accordance with the teaching of Example 2A–C except that plasmid pIJ2, disclosed in Thompson et al., 1980, Nature 286:525, was used in place of plasmid pIJ6. The desired plasmid pLR1 was suspended in TE buffer.

EXAMPLE 5

Construction of E. coli K12 HB101/pLR1

The desired construction was carried out in substantial accordance with the teaching of Example 3 except that plasmid pLR1, rather than plasmid pLR2, was used for transformation. Surviving colonies were selected and tested for the expected phenotype (Amp$^R$, Tet$^S$), and constituted the desired E. coli K12 HB101/pLR1 transformants.

EXAMPLE 6

Construction of Plasmids pEL107 and pEL105

A. BamHI Digestion of Plasmid pLR2 and Isolation of the ~1.6 kb Thiostrepton Resistance Conferring Fragment About 50 µg. of plasmid pLR2 DNA, 10 µl. reaction mix*, 10 µl. BSA (1 mg./ml.), 29 µl. water, 1 µl. (4 units/µl) of BamHI restriction enzyme were incubated at 37° C. for 2 hours. After adding an equal volume of 4M ammonium acetate and 2.5 volumes of 95% ethanol, the mixture was cooled at −20° C. for about 18 hours to precipitate the DNA. The DNA precipitate was collected by centrifugation and then suspended in about 50 µl. of TE buffer. The desired ~1.6 kb BamHI restriction fragment was isolated conventionally from the DNA suspension by gel electrophoresis. Following isolation, the fragment was resuspended in about 20 µl. of TE buffer for subsequent ligation.

*Reaction mix for BamHI restriction enzyme was prepared with the following composition. 1.5M NaCl, 60mM Tris-HCl, p$^H$7.9, 60mM MgCl$_2$.

B. Partial BamHI Digestion of Plasmid pEL103

About 20 µg. of plasmid pEL103 DNA, 10 µl. reaction mix, 10 µl. BSA (1 mg./ml.), 39 µl. water, and 1 µl. of BamHI restriction enzyme (prepared by diluting 2 µl. of enzyme in 8 µl. of water) were incubated at ambient temperature for about 15 minutes. After adding an equal volume of 4M ammonium acetate and 2 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 50 μl. of TE buffer.

C. Ligation

A mixture of about 20 μg. of the partially digested plasmid pEL103 DNA, 10 μg. of the ~1.6 kb BamHI restriction fragment of plasmid pLR2, 5 μl. ligation mix, 5 μl. BSA (1 mg./ml.), 10 μl. water, and 1 μl. T4 DNA ligase were incubated at about 16° C. for about 4 hours. After adding 40 μl. of 4M ammonium acetate and 200 μl. of cold ethanol, the mixture was cooled to −20° C. for about 18 hours to precipitate the DNA. The DNA precipitate was collected by centrifugation, washed with 70% ethanol, collected again, and then suspended in 50 μl. of medium P (Hopwood and Wright 1978, J. Molecular and General Genetics 162:307) for subsequent transformation.

Figure 8:
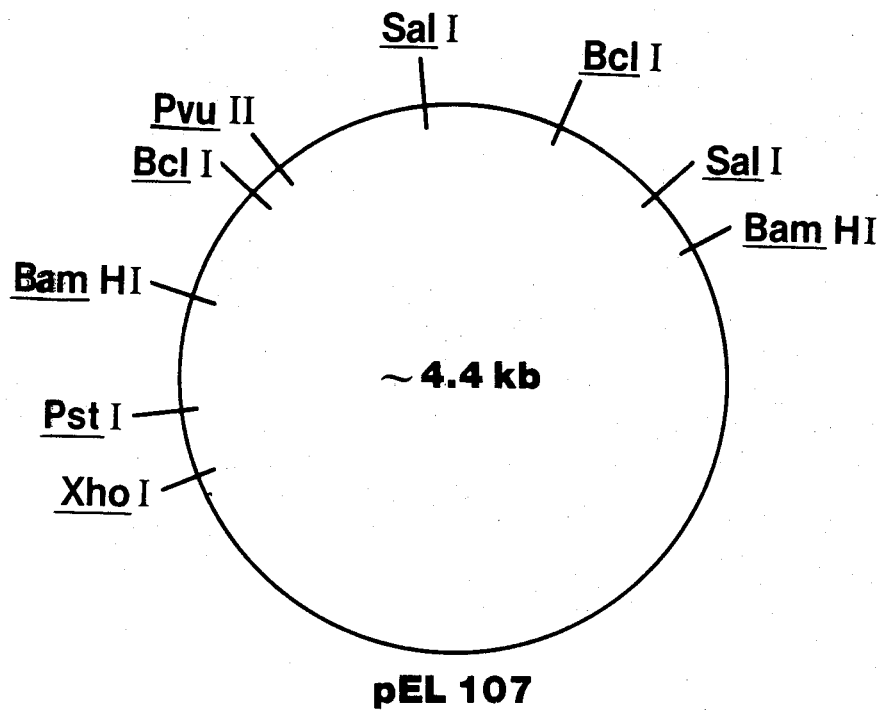
Figure 8:
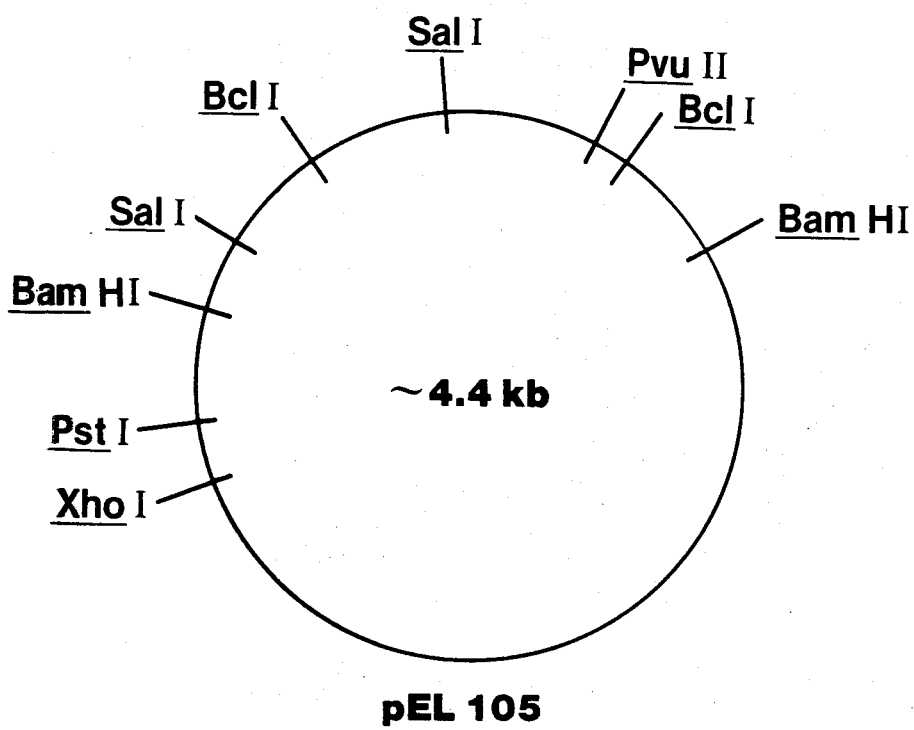

Recombinant plasmids of various types result depending upon which of the possible pEL103 restriction fragments becomes ligated to the ~1.6 kb BamHI thiostrepton resistance conferring fragment. Ligation to the ~2.8 kb BamHI restriction fragment of plasmid pEL103 results in the desired ~4.4 kb plasmids pEL107 and pEL105. Recombinant plasmids of two orientations result because the ~1.6 kb BamHI resistance conferring fragment can be oriented in either direction. A restriction site and functional map of each of plasmids pEL107 and pEL105 is presented in FIG. 8 of the accompanying drawings.

Those skilled in the art will recognize and understand that the partial BamHI digestion of plasmid pEL103 produces a mixture of different restriction fragments that can be ligated with each other and also with one or more resistance conferring DNA fragments to produce several additional recombinant plasmids. Any additional plasmids that contain the ~2.8 kb BamHI origin of replication containing fragment can also be used to further exemplify the construction of the present invention. The aforementioned additional plasmids can be conventionally transformed into appropriate host cells and then identified by restriction enzyme and gel electrophoretic analysis.

EXAMPLE 7

Construction of *Streptomyces ambofaciens*/pEL107 and *S. ambofaciens*/pEL105

Using about 20 μg. of the DNA from Example 6C and 1×10⁹ protoplasts (prepared according to Baltz, 1978, J. of General Microbiology 107:93) of *Streptomyces ambofaciens*, a strain deposited and made part of the permanent stock culture collection of the Northern Regional Research Laboratory, Peoria, Ill., from which it is available to the public under the accession number NRRL 2420, the desired constructions were made in substantial accordance with the teaching of International Publication (of International patent application No. PCT/GB79/0095) No. WO79/01169, Example 2. The desired transformants were selected for thiostrepton resistance by overlaying the regenerating protoplasts with modified R2 medium (Baltz, 1978, J. of General Microbiology 107:93) top agar containing sufficient thiostrepton to bring the final plate concentration to 50 μg./ml. The resultant *Streptomyces ambofaciens*/pEL107 and *S. ambofaciens*/pEL105 thiostrepton resistant colonies were isolated according to known procedures, cultured, and then identified by restriction enzyme and gel electrophoretic analysis of the constitutive plasmids.

Accordingly, vegetative inocula (10 ml.) of different isolated colonies are conventionally prepared by inoculating trypticase soy broth containing sufficient thiostrepton to bring the final concentration to 50 μg./ml. Several inocula are prepared and the following procedure performed until all the desired transformant types and constitutive plasmids are isolated. Thus, after cells are incubated at 30° C. until fully grown, 6 ml. of the cell containing broth are centrifuged. The resultant pellet is washed in TE buffer, pelleted again, and then suspended in 400 μl 50 mM Tris, pH 8.0. Next, about 80 μl. of 0.25 M EDTA, 20 μl. RNase, and 100 μl. (10 mg./ml. in TE) lysozyme are added. After the mixture is incubated at 37° C. for about 15 minutes, about 10 μl. of 10% Triton X-100 and 150 μl. 5 M NaCl are added followed by a final incubation at 60° C. for 15 minutes. The resultant lysate is centrifuged (15 minutes, 4° C., 15,000 rpm) and then the supernatant is conventionally extracted twice with phenol, once with a chloroform-isoamyl alcohol solution (24:1), and then ethanol precipitated. The identity of the constitutive plasmids and thus the transformants is determined conventionally by restriction enzyme and gel electrophoretic analysis.

EXAMPLE 8

Construction of Plasmids pEL109 and pEL110

A. Partial BamHI Digestion of Plasmid pLR1 and Isolation of the ~3.4 kb Neomycin Resistance Conferring Fragment The desired partial digestion and isolation are carried out in substantial accordance with the teaching of Example 6B. The ~3.4 kb BamHI restriction fragment is suspended in about 20 μl. of TE buffer for subsequent ligation.

B. Ligation

The ~3.4 kb BamHI neomycin resistance conferring restriction fragment is ligated to partially BamHI digested plasmid pEL103 (prepared in Example 6B) in substantial accordance with the teaching of Example 6C.

Figure 9:
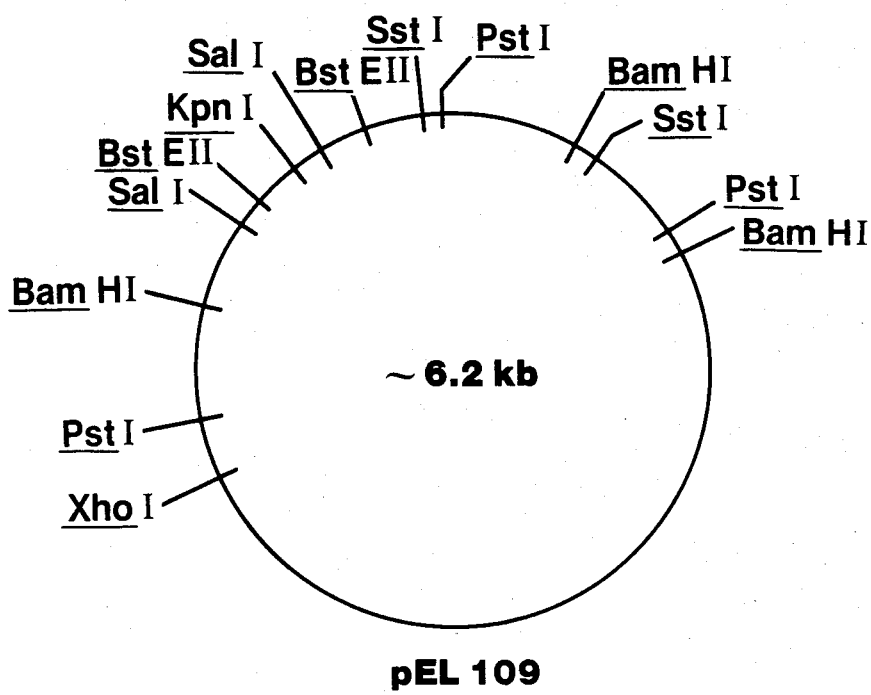
Figure 9:
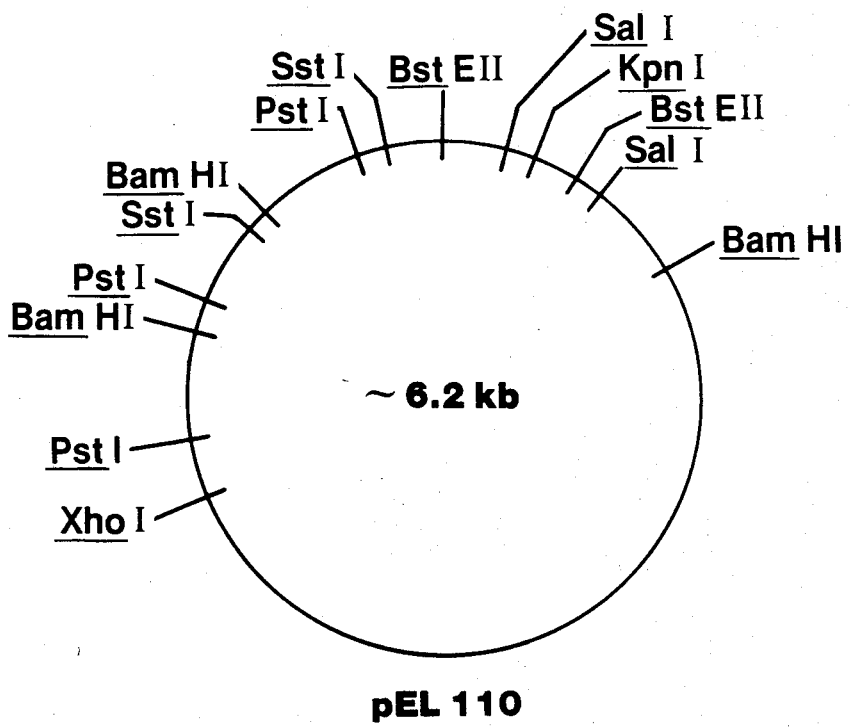

Recombinant plasmids of various types result depending upon which of the possible pEL103 restriction fragments becomes ligated to the ~3.4 kb BamHI neomycin resistance conferring fragment. Ligation to the ~2.8 kb BamHI restriction fragment of plasmid pEL103 results in the desired ~6.2 kb plasmids pEL109 and pEL110. Recombinant plasmids of two orientations result because the ~3.4 kb BamHI resistance conferring fragment can be oriented in either direction. A restriction site and functional map of each of plasmids pEL109 and pEL110 is presented in FIG. 9 of the accompanying drawings.

Those skilled in the art will recognize and understand, as described in Example 6C, that additional recombinant plasmids containing the ~2.8 kb BamHI origin of replication containing fragment can be generated by the above procedure. These plasmids can be used to further exemplify the construction of the present invention. The aforementioned additional plasmids can be conventionally transformed and then identified by restriction enzyme and gel electrophoretic analysis.

EXAMPLE 9

Construction of *Streptomyces ambofaciens*/pEL109 and *S. ambofaciens*/pEL110

Using about 20 μg. of the DNA from Example 8 and 1×10⁸ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected for neomycin resistance by overlaying the regenerating protoplasts with modified R2 medium top agar containing sufficient neomycin* to bring the final plate concentration to 1 μg./ml.
*Antibiotic neomycin can be obtained from Sigma, St. Louis, Mo.

The resultant *Streptomyces ambofaciens*/pEL109 and *S. ambofaciens*/pEL110 neomycin resistant colonies are isolated according to known procedures cultured, and then identified by restriction enzyme and gel electrophoretic analysis of the constitutive plasmids. The identity of the constitutive plasmids and thus the transformants is determined in substantial accordance with the teaching of Example 7 except that neomycin (1 μg./ml.), rather than thiostrepton, is added to the trypticase soy broth.

EXAMPLE 10

Construction of Plasmids pEL113 and pEL114

Figure 10:
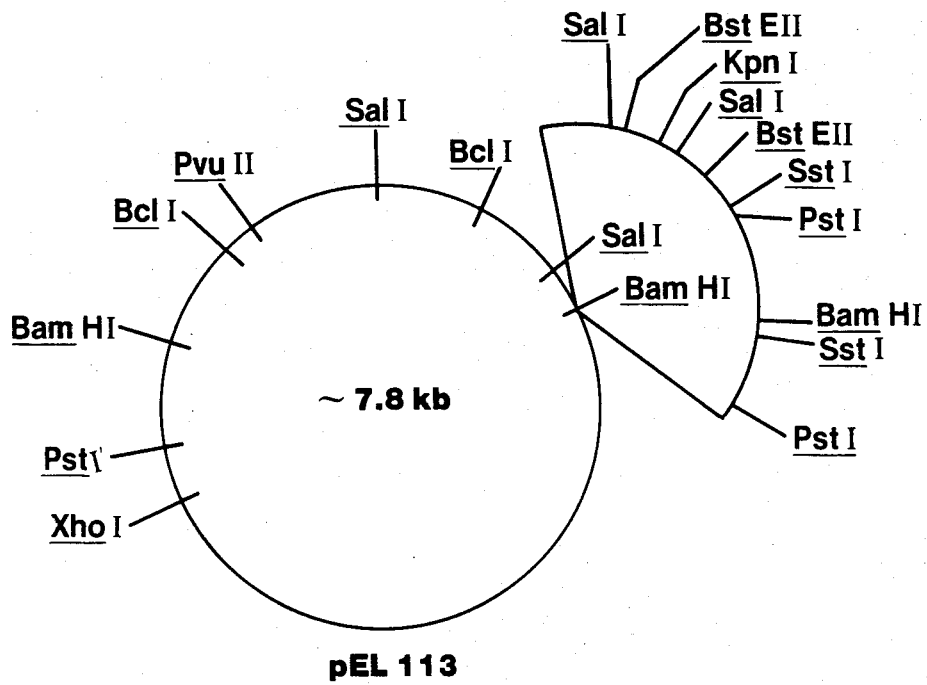
Figure 10:
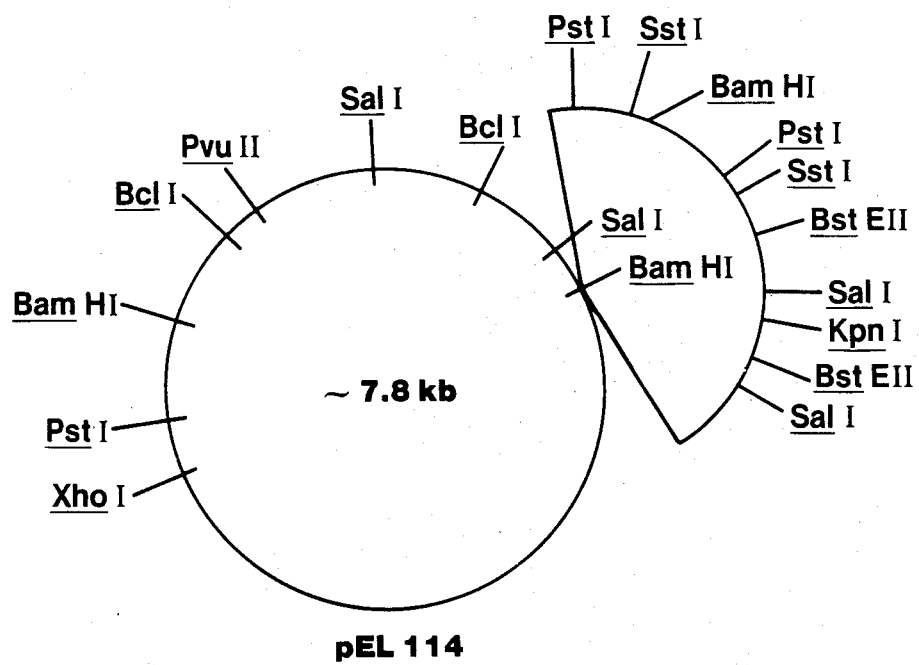

Plasmid pEL107 is isolated from *Streptomyces ambofaciens*/pEL107 (prepared in Example 7) according to the procedure of Example 1 and then is partially digested with BamHI restriction enzyme in substantial accordance with the teaching of Example 6B. The partial BamHI digest is then ligated, in substantial accordance with the teaching of Example 6C, with the ~3.4 kb neomycin resistance conferring BamHI fragment (prepared in Example 8A) of plasmid pLR1 to produce the desired plasmids. The insertional isomers of plasmids pEL113 and pEL114 are also produced since plasmid pEL107 has more than a single BamHI restriction site for the insertion of the neomycin resistance fragment. Recombinant plasmids of two orientations result because the ~3.4 kb BamHI neomycin resistance conferring fragment can be oriented in either direction. A restriction site and functional map of each of plasmids pEL113 and pEL114 is presented in FIG. 10 of the accompanying drawings.

EXAMPLE 11

Construction of *Streptomyces ambofaciens*/pEL113 and *S. ambofaciens*/pEL114

Using 20 μg. of the DNA from Example 10 and 1×10⁸ protoplasts of *Streptomyces ambofaciens* (NRRL No. 2420), the desired constructions are made in substantial accordance with the teaching of International Publication (of International Patent Application No. PCT/GB79/00095) No. WO79/01169, Example 2. The desired transformants are selected first for thiostrepton resistance and then for neomycin resistance by the methods described in Examples 7 and 9 above. The resultant *Streptomyces ambofaciens*/pEL113 and *S. ambofaciens*/pEL114 thiostrepton and neomycin resistant colonies are isolated according to known procedures, cultured, and then identified by restriction enzyme and gel electrophoretic analysis of the constitutive plasmids. The identity of the constitutive plasmids and thus the transformants is determined in substantial accordance with the teaching of Example 7 except that neomycin (1 μg./ml.) and thiostrepton (50 μg./ml.) are both added to the trypticase soy broth.

EXAMPLE 12

Construction of Plasmids pEL115 and pEL116

Figure 11:
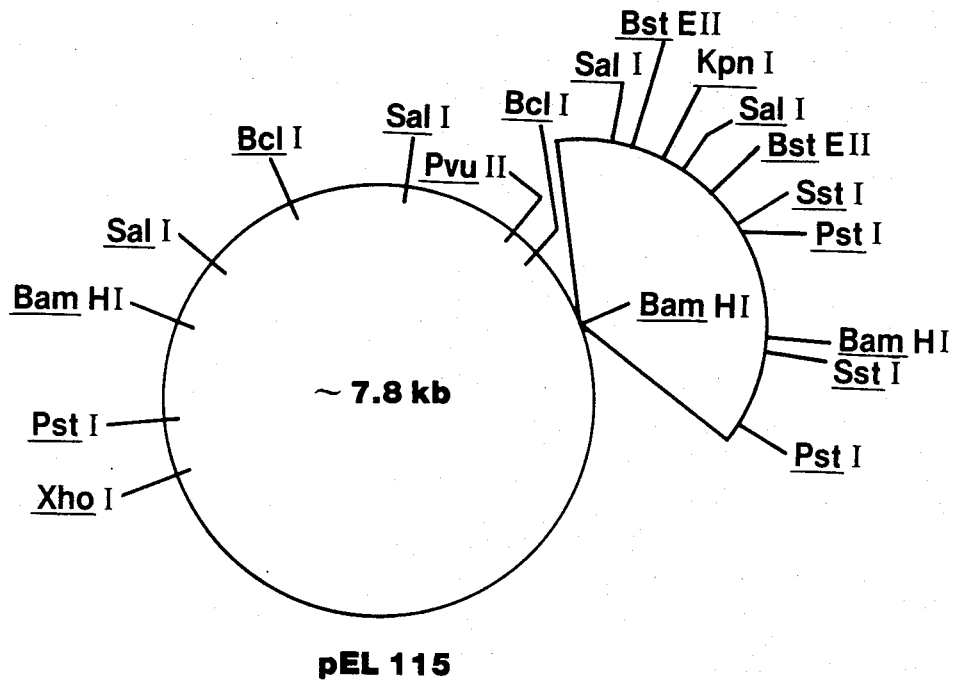
Figure 11:
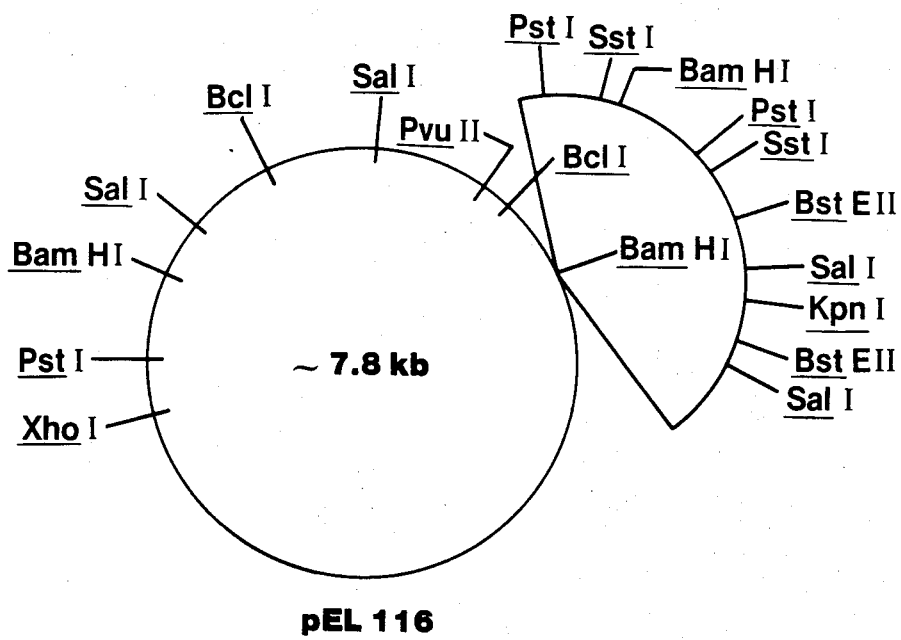

The desired plasmids are constructed in substantial accordance with the teaching of Example 10 with the exception that plasmid pEL105, rather than plasmid pEL107, is used in the partial BamHI digestion. The insertional isomers of plasmids pEL115 and pEL116 are also produced since plasmid pEL105 has more than a single BamHI restriction site for the insertion of the neomycin resistance fragment. Recombinant plasmids of two orientations result because the ~3.4 kb BamHI neomycin resistance conferring fragment can be oriented in either direction. A restriction site and functional map of each of plasmids pEL115 and pEL116 is presented in FIG. 11 of the accompanying drawings.

EXAMPLE 13

Construction of *Streptomyces ambofaciens*/pEL115 and *S. ambofaciens*/pEL116

Using 20 μg of the DNA from Example 12, the desired constructions are made in substantial accordance with the teaching of Example 11. The resultant *Streptomyces ambofaciens*/pEL115 and *S. ambofaciens*/pEL116 thiostrepton and neomycin resistant colonies are isolated according to known procedures, cultured, and then identified by restriction enzyme and gel electrophoretic analysis of the constitutive plasmids in substantial accordance with the teaching of Example 11.

EXAMPLE 14

Construction of Plasmids pEL121 and pEL122

Figure 12:
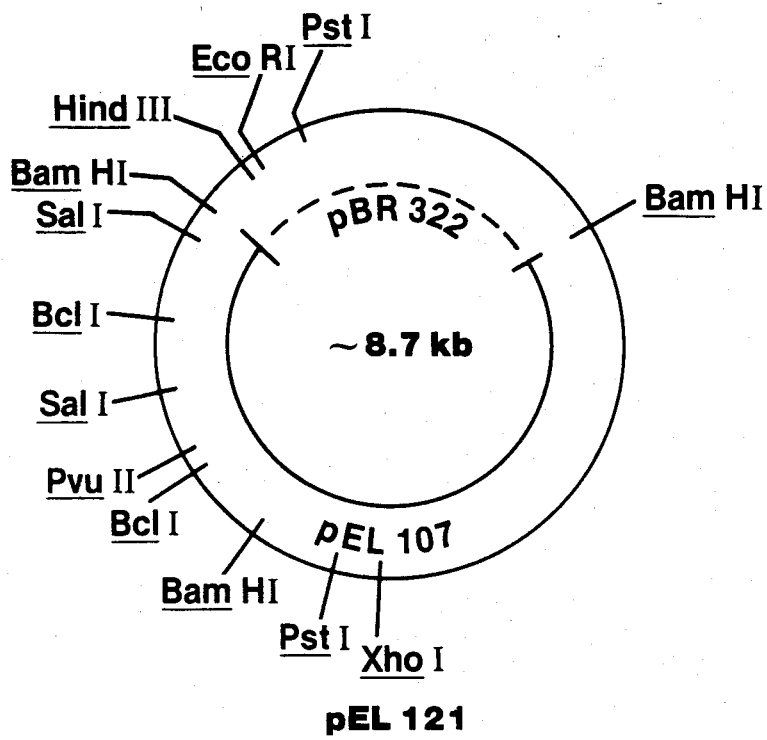
Figure 12:
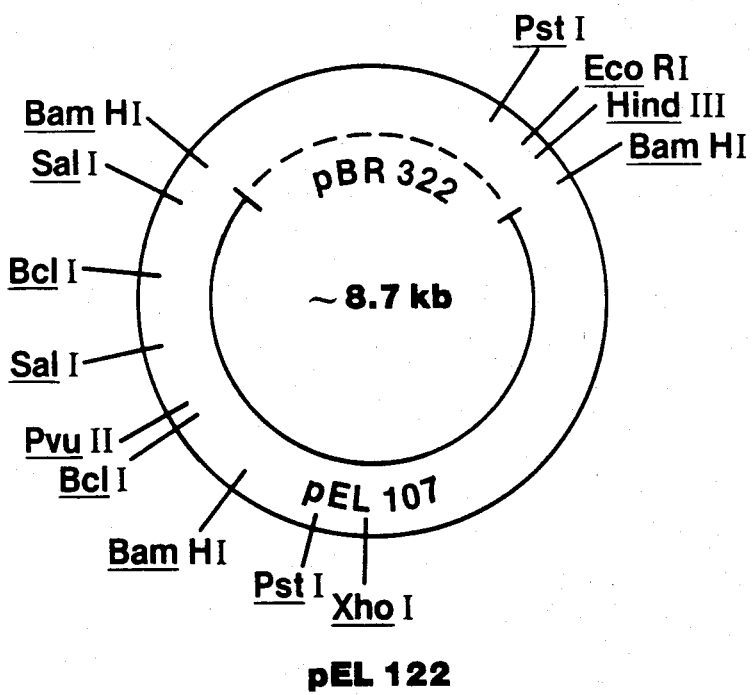
Figure 13:
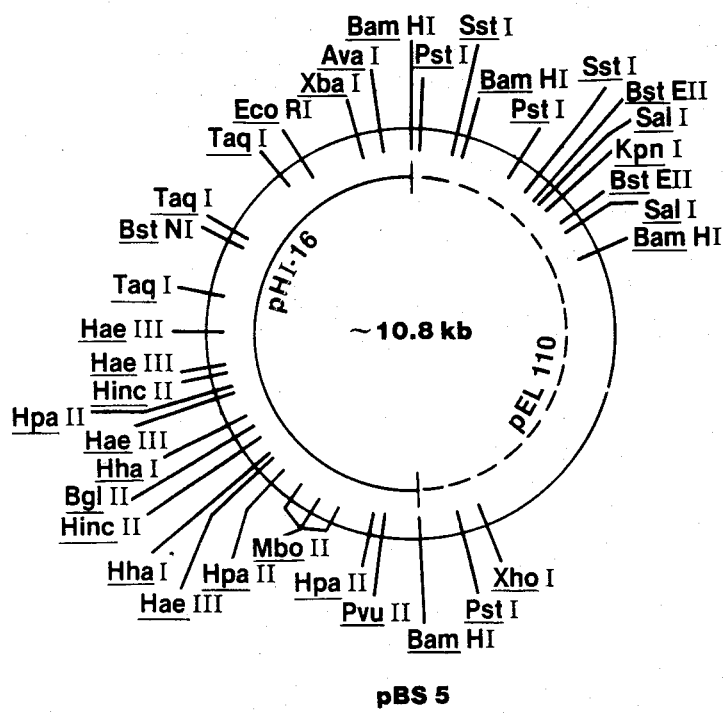
Figure 13:
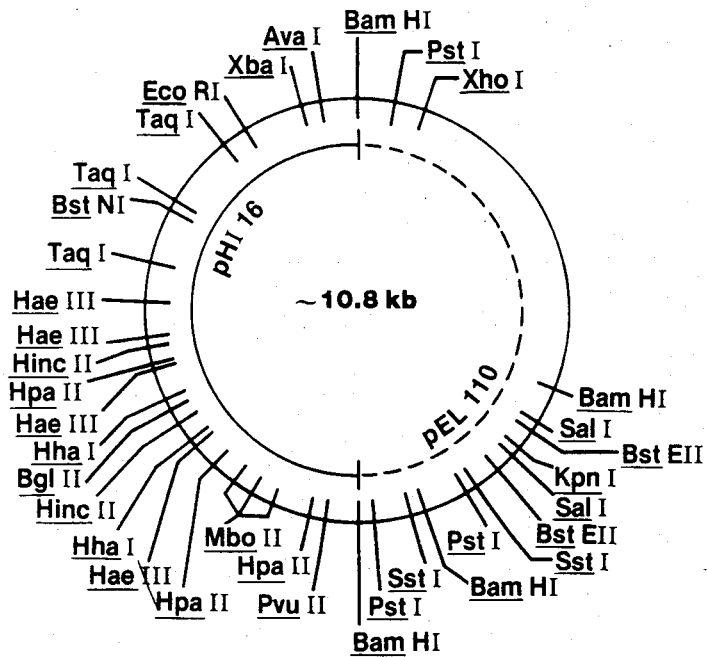
Figure 14:
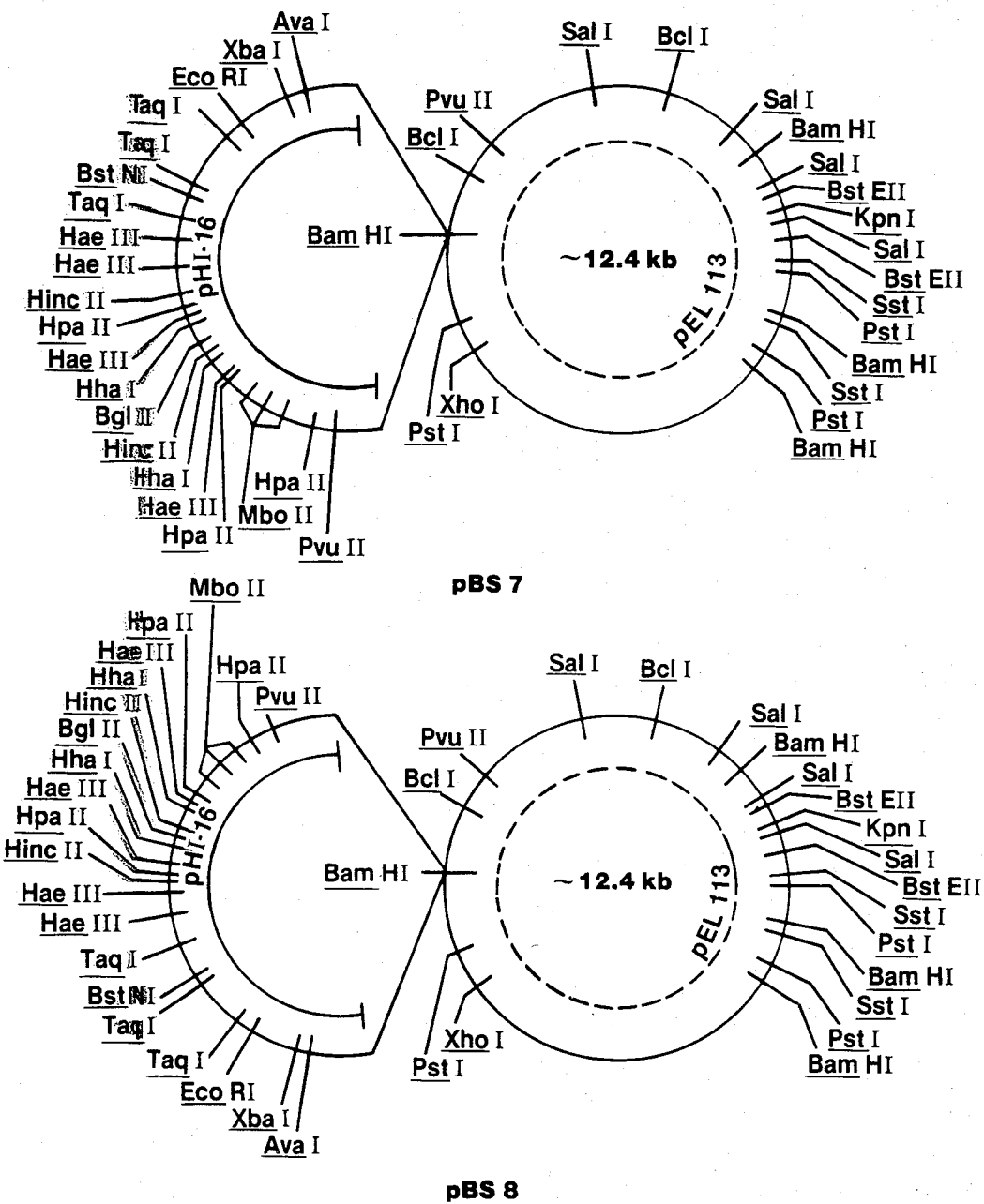

The desired plasmids are obtained by ligating a partial BamHI digest of plasmid pEL107 onto BamHI digested plasmid pBR322 in substantial accordance with the ligation procedure of Example 6C. Plasmid pEL107 is isolated from *Streptomyces ambofaciens*/pEL107 (prepared in Example 7) in substantial accordance with the teaching of Example 1 and then partially BamHI digested according to the procedure of Example 6B. The BamHI digested plasmid pBR322 is prepared in substantial accordance with the procedure of Example 2B with the exception that BamHI, rather than HindIII, restriction enzyme is used. The desired plasmid DNA is collected by centrifugation, washed with 70% ethanol, dried in vacuo, and then suspended in 50 μl. of TE buffer. In addition, the insertional isomers of plasmids pEL121 and pEL122 are also produced since plasmid pEL107 has more than a single BamHI restriction site for the insertion of the restricted plasmid pBR322. Recombinant plasmids of two orientations result because the restricted plasmid pBR322 can be oriented in either direction. A restriction site and functional map of each of plasmids pEL121 and pEL122 is presented in FIG. 12 of the accompanying drawings.

EXAMPLE 15

Construction of *E. coli* K12 HB101/pEL121 and *E. coli* K12 HB101/pEL122

The desired constructions are made in substantial accordance with the teaching of Example 3 with the exception that plasmids pEL121 and pEL122, rather than plasmid pLR2, are used for the transformation. Surviving colonies are first selected, tested for the expected phenotype (Amp$^R$, Tet$^S$), and then conventionally identified as the desired *E. coli* K12 HB101/pEL121 and *E. coli* K12 HB101/pEL122 transformants by restriction enzyme and gel electrophoretic analysis of the constitutive plasmids.

EXAMPLE 16

Isolation of Plasmid pHI-16

A. Culture of *Bacillus subtilis* MI112/pHI-16

A vegetative culture of *Bacillus subtilis* MI112/pHI-16 (NRRL B-12597) was conventionally prepared by plating on PAB agar (PAB* [Penassay broth] containing agar at 15 g./l. and chloramphenicol at 10 μg./ml.). After the inoculated plate was incubated at 37° C. for about 18 hours, a single colony was selected and used for inoculating 500 ml. of sterilized PAB medium with 10 μg./ml. chloramphenicol. The resultant inoculated broth was incubated at 37° C. for about 18 hours afterwhich the resultant *Bacillus subtilis* MI112/pHI-16 cells were ready for harvest and subsequent isolation of plasmid DNA.
*PAB can be obtained from Difco Laboratories, Detroit Mich.

B. Plasmid Isolation

About 10 g. (wet wgt) of *Bacillus subtilis* MI112/pHI-16 cells were first harvested by centrifugation (10 minutes, 4° C., 10,000 rpm), then washed in about 50 ml. TES, and finally collected again by centrifugation. About 20 ml. TE buffer with 25% sucrose were added to the pellet followed by about 10 mg. of lysozyme in 250 μl. water. The mixture was then incubated at 37° C. for about 30 minutes afterwhich about 100 units of RNase were added. The resultant mixture was incubated at 37° C. for 30 minutes and then, upon being made 1% and 1 M with respect to SDS (sodium dodecyl sulfate) and sodium chloride respectively, the mixture was cooled in an ice bath for about 3 hours. After the lysate was centrifuged (30 minutes, 4° C., 19,000 rpm), the supernatent was adjusted to 31.8 ml. with TE, followed by addition of 28.7 g. of cesium chloride and 0.4 ml. (10 mg./ml.) of ethidium bromide. A cesium chloride gradient was established by centrifuging at 49,500 rpm for 16 hours. The plasmid band was collected and centrifuged at 55,000 rpm for 16 hours, then collected again, extracted thrice with equal volumes of isoamyl alcohol, dialyzed against dilute TE, ethanol precipitated, and resuspended in 400 μl. of TE. The resultant plasmid pHI-16 DNA was stored at 4° C. for future use.

The kanamycin resistance gene is contained within the ~0.74 kb HpaII fragment of plasmid pHI-16. Therefore, treatment with HpaII restriction enzyme followed by ligation results in a ~3.9 kb plasmid, designated herein as pHI-18, which lacks the kanamycin resistance gene. A detailed procedure for constructing plasmid pHI-18 is described below.

EXAMPLE 17

Construction of Plasmid pHI-18

A. Partial HpaII Digestion of Plasmid pHI-16

About 5 μl. (2.5 μg.) of plasmid pHI-16 DNA, 1 μl. (2 mg./ml.) BSA, 37 μl. water, 2 μl. of HpaII (containing 2 New England Bio Labs units) restriction enzyme, and 5 μl. reaction mix* were incubated at 37° C. for 1 hour. After the reaction was terminated by heating at 65° C. for 10 minutes, the DNA was precipitated by adding 2 volumes of 95% ethanol. The resultant DNA precipitate was washed in 70% ethanol, dried in vacuo, suspended in 5 μl. of TE buffer, and stored at 4° C. for future use.
*Reaction mix for HpaII restriction enzyme was prepared with the following composition. 60 mM KCl, 100 mM Tris-HCl, pH 7.4, 100 mM MgCl$_2$, 10 mM Dithiothreitol.

B. Ligation of Plasmid pHI-16 HpaII Digest

About 5 μl. of plasmid pHI-16 HpaII digest (prepared in Example 17A), 2 μl. T4 DNA ligase, and 43 μl. ligation mix* were incubated at about 16° C. for about 18 hours. The reaction was terminated by the addition of about 5 μl. of 3 M sodium acetate and 150 μl. of 95% ethanol. The desired DNA precipitate was washed in 70% ethanol, dried in vacuo, suspended in 10 μl. of TE buffer, and stored at 4° C. for future use.
*Ligation mix was prepared with the following composition. 66 mM Tris-HCl, pH 7.8, 10 mM Dithiothreitol, 6.6 mM MgCl$_2$, 4 mM ATP.

EXAMPLE 18

Construction of *Bacillus subtilis* MI112/pHI-18

*Bacillus subtilis* MI112 can be obtained by conventionally culturing *B. subtilis* MI112/pHI-16 (NRRL B-12597) in the absence of chloramphenicol. The *B. subtilis* MI112/pHI-16 cells spontaneously lose the pHI-16 plasmid under the aforementioned culture conditions thus generating the desired chloramphenicol sensitive *B. subtilis* MI112 strain. Those skilled in the art will recognize and understand that sensitivity to chloramphenicol can be employed for testing and insuring that only *B. subtilis* MI112 cells that lack the plasmid are selected and used in the Bacillus transformation procedures herein disclosed.

About 50 ml. of sterile PAB was inoculated with *Bacillus subtilis* MI112 and incubated at 37° C. until a cell density of $2 \times 10^8$ cells/ml. was reached. The cells were then protoplasted, using sterile technique, by pelleting and then resuspending the cells in about 5 ml. of SMMP (equal volumes of each of 4×PAB and a solution comprising 1.0 M sucrose, 0.04 M maleic acid, and 0.04 M MgCl$_2$, pH adjusted to 6.5 with NaOH). Next, about 250 μl. of lysozyme (20 mg./ml. in SMM [0.5 M sucrose, 0.02 M maleic acid, and 0.02 M MgCl$_2$, pH adjusted to 6.5 with NaOH]) were added using filter sterilization. The cells were incubated with gentle shaking at 37° C. for about 2 hours. The resultant protoplasts were pelleted, washed with 5 ml. SMMP, and then resuspended in 5 ml. SMMP. Following centrifugation (25° C., 12 minutes, 2,600 rpm), about 0.1 ml. of the protoplasts were transformed by adding about 20 μl. of a 1:1 mixture comprising plasmid pHI-18 DNA (prepared in Example 17) and 2×SMM. About 1.5 ml. of PEG solution (40 g. PEG 6000 [polyethyleneglycol], 50 ml. 2×SMM, and water to 100 ml.) were then immediately added and, after about 2 minutes, 5 ml. of SMMP were also added. Next, the protoplasts were pelleted, suspended in 1 ml. of SMMP, and incubated at 30° C. with gentle shaking for about 2 hours. Aliquots of the thus prepared suspension were plated on chloramphenicol containing DM3 regeneration medium which per liter had the following composition.

| | | |
|---|---|---|
| 91 g. | D-mannitol in 555 ml. deionized water containing 12 g. agar | |
| 10% | Casamino acids | 50 ml. |
| 10% | Yeast extract | 50 ml. |
| 20% | Glucose | 25 ml. |
| 5% | Dipotassium phosphate | 100 ml. |

-continued

| 1 M | MgCl₂ | 20 ml. |
| 10% | Gelatin | 200 ml. |
| 10 mg | Chloramphenicol | |

The D-mannitol, casamino acids and yeast extract were autoclaved together. The gelatin was added immediately after autoclaving and the remaining ingredients were added after the mixture had cooled. The medium had a final chloramphenicol concentration of 10 μg./ml.

The resultant chloramphenicol resistant colonies were tested for kanamycin sensitivity. A chloramphenicol resistant and kanamycin sensitive colony was selected as the desired *Bacillus subtilis* MI112/pHI-18 strain. The strain was cultured and the identity further confirmed by conventional restriction enzyme and gel electrophoretic analysis of the constitutive plasmid.

EXAMPLE 19

Construction of Plasmids pBS1 and pBS3

A. Partial BamHI Digestion of Plasmid pEL105

About 10 μl. (5 μg.) of plasmid pEL105 (conventionally isolated from *Streptomyces ambofaciens*/pEL105 [prepared in Example 7] in substantial accordance with the teaching of Example 1), 2 μl. BSA (1 mg./ml.), 29 μl. water, 1 μl. of BamHI (diluted 1:4 with water) restriction enzyme, and 5 μl. reaction mix* were incubated at 25° C. for 15 minutes. The reaction was terminated by the addition of about 50 μl. of 4 M ammonium acetate and 300 μl. of 95% ethanol. After cooling at −20° C. for about 2 hours, the resultant DNA precipitate was collected by centrifugation, washed twice in 70% ethanol, dried in vacuo, and then suspended in about 10 μl. of TE buffer. Because plasmid pEL105 has two BamHI restriction sites, a mixture of different fragments results.
*Reaction mix for BamHI restriction enzyme was prepared with the following composition. 1.5 M NaCl, 60 mM Tris-HCl, pH 7.9, 60 mM MgCl₂.

B. BamHI Digestion of Plasmid pHI-18

About 5 μl. (5 μg.) of plasmid pHI-18, 2 μl. BSA (1 mg./ml.), 9 μl. water, 1 μl. of BamHI (4 units/μl.) restriction enzyme, and 1.5 μl. reaction mix were incubated at 37° C. for about 2 hours. After adding an equal volume of 4 M ammonium acetate and 2.5 volumes of 95% ethanol, the mixture was cooled at −20° C. for about 18 hours to precipitate the DNA. The DNA precipitate was collected by centrifugation, washed in 70% ethanol, and then suspended in about 10 μl. of TE buffer.

C. Ligation

About 5 μl. of BamHI digested plasmid pHI-18 (prepared in Example 18B), 8 μl. of plasmid pEL105 BamHI partial digest (prepared in Example 18A), 27 μl. water, 5 μl. (4 mM) ATP, 5 μl. ligation mix, and 2 μl. T4 DNA ligase were incubated at 16° C. for about 18 hours. The reaction was terminated by the addition of 50 μl. 4 M ammonium acetate and 200 μl. of 95% ethanol. After incubation at −20° C. for about 2 hours, the desired plasmid pBS1 and pBS3 DNA precipitate was collected by centrifugation, washed in 70% ethanol, dried in vacuo, suspended in 10 μl. of TE buffer, and stored at 4° C. for future use.

Since plasmid pEL105 has two BamHI restriction sites, a partial BamHI digest results in two ~4.4 kb BamHI fragments. Therefore, the insertional isomers of plasmids pBS1 and pBS3 are also produced by the above procedure. Recombinant plasmids of two orientations result because the BamHI restricted DNA can be ligated in either direction. A restriction site and functional map of each of plasmids pBS1 and pBS3 is presented in FIG. 6 of the accompanying drawings.

EXAMPLE 20

Construction of Plasmids pBS2 and pBS4

The desired constructions are made in substantial accordance with the teaching of Example 19A-C except that BamHI digested plasmid pHI-16, rather than plasmid pHI-18, is used.

Since plasmid pEL105 has two BamHI restriction sites, a partial BamHI digest results in two ~4.4 kb BamHI fragments. Therefore, the insertional isomers of plasmids pBS2 and pBS4 are also produced by the above procedure. Recombinant plasmids of two orientations result because the BamHI restricted DNA can be ligated in either direction. A restriction site and functional map of each of plasmids pBS2 and pBS4 is presented in FIG. 7 of the accompanying drawings.

EXAMPLE 21

Construction of Plasmids pBS5 and pBS6

The desired constructions are made in substantial accordance with the teaching of Example 19A-C except that plasmids pEL110 and pHI-16, rather than plasmids pEL105 and pHI-18, are used. Plasmid pEL110 is conventionally isolated from *Streptomyces ambofaciens*/pEL110 (prepared in Example 9) in substantial accordance with the teaching of Example 1.

Since plasmid pEL110 has two BamHI restriction sites, a partial BamHI digest results in two ~6.2 kb BamHI fragments. Therefore, the insertional isomers of plasmids pBS5 and pBS6 are also produced by the above procedure. Recombinant plasmids of two orientations result because the BamHI restricted DNA can be ligated in either direction. A restriction site and functional map of each of plasmids pBS5 and pBS6 is presented in FIG. 13 of the accompanying drawings.

EXAMPLE 22

Construction of Plasmids pBS7 and pBS8

The desired constructions are made in substantial accordance with the teaching of Example 19A-C except that plasmids pEL113 and pHI-16, rather than plasmids pEL105 and pHI-18, are used. Plasmid pEL113 is conventionally isolated from *Streptomyces ambofaciens*/pEL113 (prepared in Example 11) in substantial accordance with the teaching of Example 1.

Since plasmid pEL113 has three BamHI restriction sites, a partial BamHI digest results in three ~7.8 kb BamHI fragments. Therefore, the insertional isomers of plasmids pBS7 and pBS8 are also produced by the above procedure. Recombinant plasmids of two orientations result because the BamHI restricted DNA can be ligated in either direction. A restriction site and functional map of each of plasmids pBS7 and pBS8 is presented in FIG. 14 of the accompanying drawings.

EXAMPLE 23

Construction of Plasmids pBS9 and pBS10

The desired constructions are made in substantial accordance with the teaching of Example 19A-C except that plasmids pEL122 and pHI-16, rather than plasmids pEL105 and pHI-18, are used. Plasmid pEL122 is isolated from *E. coli* K12 HB101/pEL122 (prepared in Example 15) according to known procedures.

Figure 15:
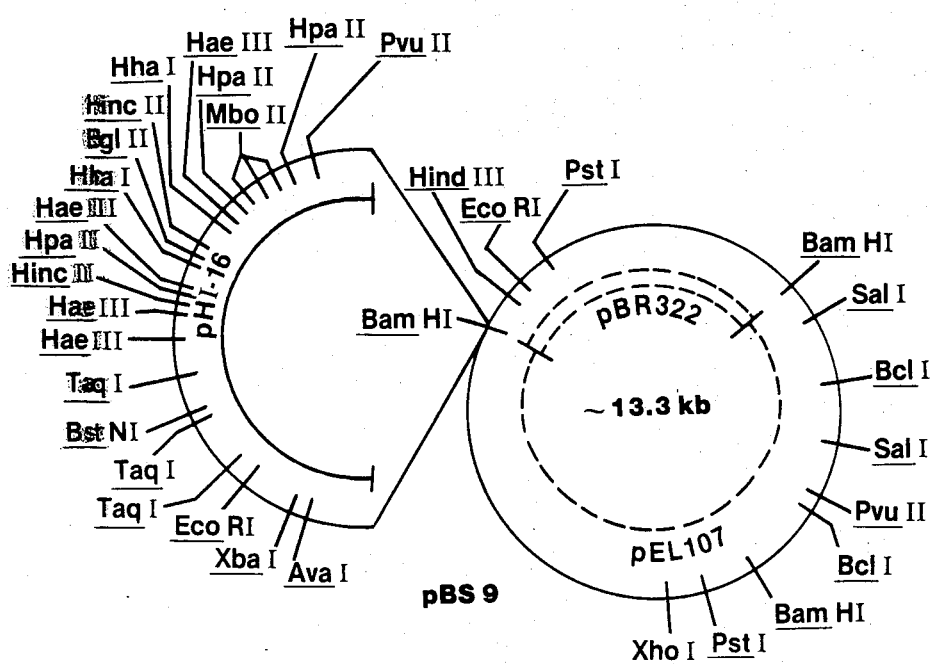
Figure 15:
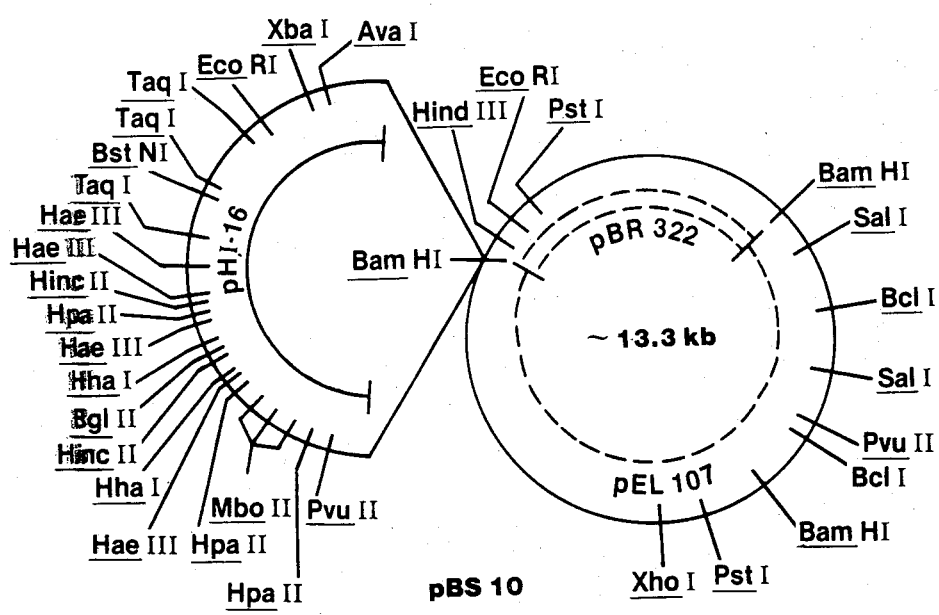

Since plasmid pEL122 has three BamHI restriction sites, a partial BamHI digest results in three ~8.7 kb BamHI fragments. Therefore, the insertional isomers of plasmids pBS9 and pBS10 are also produced by the above procedure. Recombinant plasmids of two orientations result because the BamHI restricted DNA can be ligated in either direction. A restriction site and functional map of each of plasmids pBS9 and pBS10 is presented in FIG. 15 of the accompanying drawings.

EXAMPLE 24

Construction of *Bacillus subtilis* MI112/pBS1 and *Bacillus subtilis* MI112/pBS3

The desired constructions are made in substantial accordance with the teaching of Example 18 except that DNA comprising plasmids pBS1 and pBS3 (prepared in Example 19), rather than plasmid pHI-18, is used. The resultant *Bacillus subtilis* MI112/pBS1 and *Bacillus subtilis* MI112/pBS3 chloramphenicol resistant and kanamycin sensitive transformant colonies are isolated according to known procedures, cultured, and then conventionally identified by restriction enzyme and gel electrophoretic analysis of the constitutive plasmids.

EXAMPLE 25

Construction of *Bacillus subtilis* MI112/pBS2 and *Bacillus subtilis* MI112/pBS4

The desired constructions are made in substantial accordance with the teaching of Example 18 except that DNA comprising plasmids pBS2 and pBS4 (prepared in Example 20), rather than plasmid pHI-18, is used. The resultant chloramphenicol resistant colonies were selected and conventionally tested for kanamycin resistance. The chloramphenicol and kanamycin resistant *Bacillus subtilis* MI112/pBS2 and *B. subtilis* MI112/pBS4 transformants are isolated according to known procedures, cultured, and then conventionally identified by restriction enzyme and gel electrophoretic analysis of the constitutive plasmids.

EXAMPLE 26

Construction of *Bacillus subtilis* MI112/pBS5 and *Bacillus subtilis* MI112/pBS6

The desired constructions are made in substantial accordance with the teaching of Example 18 except that DNA comprising plasmids pBS5 and pBS6 (prepared in Example 21), rather than plasmid pHI-18, is used. The resultant chloramphenicol resistant colonies are selected and conventionally tested for kanamycin resistance. The chloramphenicol and kanamycin resistant *Bacillus subtilis* M112/pBS5 and *B. subtilis* MI112/pBS6 transformants are isolated according to known procedures, cultured, and then conventionally identified by restriction enzyme and gel electrophoretic analysis of the constitutive plasmids.

EXAMPLE 27

Construction of *Bacillus subtilis* MI112/pBS7 and *Bacillus subtilis* MI112/pBS8

The desired constructions are made in substantial accordance with the teaching of Example 18 except that DNA comprising plasmids pBS7 and pBS8 (prepared in Example 22), rather than plasmid pHI-18, is used. The resultant chloramphenicol resistant colonies are selected and conventionally tested for kanamycin resistance. The chloramphenicol and kanamycin resistant *Bacillus subtilis* MI112/pBS7 and *B. subtilis* M112/pBS8 transformants are selected according to known procedures, cultured, and then conventionally identified by restriction enzyme and gel electrophoretic analysis of the constitutive plasmids.

EXAMPLE 28

Construction of *Bacillus subtilis* MI112/pBS9 and *Bacillus subtilis* MI112/pBS10

The desired constructions are made in substantial accordance with the teaching of Example 18 except that DNA comprising plasmids pBS9 and pBS10 (prepared in Example 23), rather than plasmid pHI-18, is used. The resultant chloramphenicol resistant colonies are selected and conventionally tested for kanamycin resistance. The putative chloramphenicol and kanamycin resistant *Bacillus subtilis* M112/pBS9 and *B. subtilis* M112/pBS10 transformants are selected according to known procedures, cultured, and then conventionally identified by restriction enzyme and gel electrophoretic analysis of the constitutive plasmids.

EXAMPLE 29

Construction of *Streptomyces ambofaciens*/pBS1 and *S. ambofaciens*/pBS3

Using about 20 μg. of the DNA from Example 19 and $1 \times 10^8$ protoplasts of *Streptomyces ambofaciens* (NRRL No. 2420), the desired constructions are made in substantial accordance with the teaching of International Publication (of International Patent Application No. PCT/GB79/00095) No. WO79/01169, Example 2. The desired transformants are selected for thiostrepton resistance by overlaying the regenerating protoplasts with modified R2 medium top agar containing sufficient thiostrepton to bring the final plate concentration to 50 μg./ml.

The resultant *Streptomyces ambofaciens*/pBS1 and *S. ambofaciens*/pBS3 thiostrepton resistant colonies are isolated according to known procedures, cultured, and then identified by restriction enzyme and gel electrophoretic analysis of the constitutive plasmids in substantial accordance with the teaching of Example 7.

EXAMPLE 30

Construction of *Streptomyces ambofaciens*/pBS2 and *S. ambofacines*/pBS4

Using about 20 μg. of the DNA from Example 20 and $1 \times 10^8$ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected for thiostrepton resistance by overlaying the regenerating protoplasts with modified R2 medium top agar containing sufficient thiostrepton to bring the final plate concentration to 50 μg./ml.

The resultant *Streptomyces ambofaciens*/pBS2 resistant colonies are isolated according to known procedures, cultured, and then identified by restriction enzyme and gel electrophoretic analysis of the constitutive plasmids in substantial accordance with the teaching of Example 7.

EXAMPLE 31

Construction of *Streptomyces ambofaciens*/pBS5 and *S. ambofaciens*/pBS6

Using about 20 μg. of the DNA from Example 21 and $1 \times 10^8$ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected for neomycin resistance by overlaying the regenerating protoplasts with modified R2 medium top agar containing sufficient neomycin to bring the final plate concentration to 1 μg./ml.

The resultant *Streptomyces ambofaciens*/pBS5 and *S. ambofaciens*/pBS6 neomycin resistant colonies are isolated according to known procedures, cultured, and then identified by restriction enzyme and gel electrophoretic analysis of the constitutive plasmids in substantial accordance with Example 9.

EXAMPLE 32

Construction of *Streptomyces ambofaciens*/pBS7 and *S. ambofaciens*/pBS8

Using about 20 μg. of the DNA from Example 22 and $1 \times 10^8$ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected first for thiostrepton resistance and then for neomycin resistance by the methods described in Examples 7 and 9 above.

The resultant *Streptomyces ambofaciens*/pBS7 and *S. ambofaciens*/pBS8 thiostrepton and neomycin resistant colonies are isolated according to known procedures, cultured, and then identified by restriction enzyme and gel electrophoretic analysis of the constitutive plasmids in substantial accordance with the teaching of Example 11.

EXAMPLE 33

Construction of *Streptomyces ambofaciens*/pBS9 and *S. ambofaciens*/pBS10

Using about 20 μg. of the DNA from Example 23 and $1 \times 10^8$ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected for thiostrepton resistance by overlaying the regenerating protoplasts with modified R2 medium top agar containing sufficient thiostrepton to bring the final plate concentration to 50 μg./ml.

The resultant *Streptomyces ambofaciens*/pBS9 and *S. ambofaciens*/pBS10 thiostrepton resistant colonies are isolated according to known procedures, cultured, and then identified by restriction enzyme and gel electrophoretic analysis of the constitutive plasmids in substantial accordance with the teaching of Example 7.

EXAMPLE 34

Construction of *E. coli* K12 HB101/pBS9 and *E. coli* K12 HB101/pBS10

The desired constructions are made in substantial accordance with the teaching of Example 3 with the exception that DNA prepared in Example 23, rather than plasmid pLR2, is used for the transformation. Surviving colonies are first selected, tested for the expected phenotype ($Amp^R$, $Tet^S$), and then conventionally identified as the desired *E. coli* K12 HB101/pBS9 and *E. coli* K12 HB101/pBS10 transformants by restriction enzyme and gel electrophoretic analysis of the constitutive plasmids.

Representative plasmids and transformants that can be constructed according to the foregoing teaching are respectively shown in Tables I and II below. For purposes of the present invention, the pBS plasmids named in Table 1 also include any insertional isomers resulting from a particular construction.

TABLE 1

| Example No. | Representative Plasmids | |
|---|---|---|
| | Plasmid Name* | Construction |
| | | Ligation of BamHI Fragments |
| 35 | pBS11 and pBS12 | pHI-16 and pEL107 |
| 36 | pBS13 and pBS14 | pHI-16 and pEL109 |
| 37 | pBS15 and pBS16 | pHI-16 and pEL114 |
| 38 | pBS17 and pBS18 | pHI-16 and pEL115 |
| 39 | pBS19 and pBS20 | pHI-16 and pEL116 |
| 40 | pBS21 and pBS22 | pHI-16 and pEL121 |
| 41 | pBS23 and pBS24 | pHI-18 and pEL107 |
| 42 | pBS25 and pBS26 | pHI-18 and pEL109 |
| 43 | pBS27 and pBS28 | pHI-18 and pEL110 |
| 44 | pBS29 and pBS30 | pHI-18 and pEL113 |
| 45 | pBS31 and pBS32 | pHI-18 and pEL114 |
| 46 | pBS33 and pBS34 | pHI-18 and pEL115 |
| 47 | pBS35 and pBS36 | pHI-18 and pEL116 |
| 48 | pBS37 and pBS38 | pHI-18 and pEL121 |
| 49 | pBS39 and pBS40 | pHI-18 and pEL122 |
| 50 | pBS41 and pBS42 | pBR322 and pBS13 |
| 51 | pBS43 and pBS44 | pBR322 and pBS18 |
| 52 | pBS45 and pBS46 | pBR322 and pBS7 |
| 53 | pBS47 and pBS48 | pBR322 and pBS27 |
| 54 | pBS49 and pBS50 | pBR322 and pBS2 |
| 55 | pBS51 and pBS52 | pBR322 and pBS1 |
| 56 | pBS53 and pBS54 | pBR328 and pBS2 |
| 57 | pBS55 and pBS56 | pBR328 and pBS1 |
| | | Ligation of EcoRI Fragments |
| 58 | pBS57 and pBS58 | pBR328 and pBS2 |
| 59 | pBS59 and pBS60 | pBR328 and pBS1 |

*The first named plasmid, in Examples 35–49 above, designates the orientation in which the pEL thiostrepton or neomycin resistance gene is opposite (rather than adjacent to) the pHI kanamycin or chloramphenicol resistance gene. The second plasmid designates the reverse orientation.
The first named plasmid, in Examples 50–57 above, designates the orientation in which the pHI PvuII site is adjacent to the pBR HindIII site. The second plasmid designates the reverse orientation.
The first named plasmid, in Examples 58–59 above, designates the orientation in which the pHI XbaI site is adjacent to the pBR PvuII site. The second plasmid designates the reverse orientation.

TABLE II

Representative Transformants

1. Bacillus R/pR[1] wherein R is *subtilis, subtilis* MI112, RUB331, *thuringiensis, megaterium, cereus, popillae, laterosporus,* or *amyloliquifaciens* and R[1] independently is any pBS plasmid herein named in Examples 35–59 of Table 1.

2. Streptomyces R²/pR¹ wherein R² is *ambofaciens, fradiae, coelicolor, aureofaciens, granuloruber,* or *lividans* and R¹ independently is as defined above.

3. *E. coli* R³/pR⁴ wherein R³ is K12, K12 HB101, K12 RV308, C600R$_k$—M$_k$—, or K12 C600 and R⁴ independently is any pBS plasmid herein named in Examples 48–59 of Table 1.

We claim:

1. A multifunctional recombinant DNA cloning vector comprising:
    (a) two or more functionally different origins of replication that are independently selected from the group consisting of any origin of replication that is functional in Streptomyces, any origin of replication that is functional in Bacillus, and any origin of replication that is functional in *E. coli*, and .
    (b) one or more DNA segments that confer resistance to at least one antibiotic when transformed into a sensitive host cell in which an origin of replication comprising said vector is functional, said host cells being susceptible to transformation, cell division, and culture, subject to the limitation that when said vector is limited to two functionally different origins of replication, neither of the origins of replication is functional in *E. coli*.

2. The cloning vector of claim 1 wherein the origins of replication that are functional in Streptomyces, Bacillus, and *E. coli* are respectively a restriction fragment of plasmid pEL103, a restriction fragment of plasmid pHI-16, and a restriction fragment of an *E. coli* plasmid.

3. The cloning vector of claim 1 wherein the origins of replication in said vectors are limited to a restriction fragment of plasmid pEL103 and a restriction fragment of plasmid pHI-16.

4. The cloning vector of claim 1, 2 or 3 wherein one DNA segment conveys resistance to thiostrepton.

5. The cloning vector of claim 1, 2 or 3 wherein one DNA segment conveys resistance to neomycin.

6. The cloning vector of claim 1, 2 or 3 wherein one DNA segment conveys resistance to chloramphenicol.

7. The cloning vector of claim 1, 2 or 3 wherein one DNA segment conveys resistance to kanamycin.

8. The cloning vector of claim 2 wherein one DNA segment conveys resistance to ampicillin.

9. The cloning vector of claim 4 wherein the DNA segment is the ~1.6 kb BamHI restriction fragment of plasmid pLR2.

10. The cloning vector of claim 5 wherein the DNA segment is the ~3.4 kb BamHI restriction fragment of plasmid pLR1.

11. The cloning vedtor of claim 6 wherein the DNA segment is the ~4.6 kb BamHI restriction fragment of plasmid pHI-16.

12. The cloning vector of claim 7 wherein the DNA segment is the ~3.9 kb BamHI restriction fragment of plasmid pHI-18.

13. The cloning vector of claim 1, 2 or 3 wherein the one or more DNA segments that convey antibiotic resistance are selected from the group consisting of segments that convey resistance to hygromycin, viamycin, tylosin, erythromycin, streptomycin, and bacteriocin.

14. The cloning vector of claim 3 wherein the origin of replication containing restriction fragment of plasmid pEL103 is the ~2.8 kb BamHI fragment.

15. The cloning vector of claim 2 in which the *E. coli* plasmid is selected from the group of plasmids consisting of pBR322 and pBR328.

16. The cloning vector of claim 1 which is selected from the group of plasmids consisting of PBS1, pBS2, pBS3, pBS4, pBS5, pBS6, pBS7, pBS8, pBS9, pBS10, pBS11, pBS12, pBS13, pBS14, pBS15, pBS16, pBS17, pBS18, pBS19, pBS20, pBS21, pBS22, pBS23, pBS24, pBS25, pBS26, pBS27, pBS28, pBS29, pBS30, pBS31, pBS32, pBS33, pBS34, pBS35, pBS36, pBS37, pBS38, pBS39, pBS40, pBS41, pBS42, pBS43, pBS44, pBS45, pBS46, pBS47, pBS48, pBS49, pBS50, pBS51, pBS52, pBS53, pBS54, pBS55, pBS56, pBS57, pBS58, pBS59, and pBS60.

17. The cloning vector of claim 16 which is plasmid pBS1.

18. The cloning vedtor of claim 16 which is pBS2.

19. The cloning vector of claim 16 which is pBS3.

20. The cloning vector of claim 16 which is pBS4.

21. The cloning vector of claim 16 which is pBS5.

22. The cloning vector of claim 16 which is pBS7.

23. The cloning vector of claim 16 which is pBS8.

24. The cloning vector of claim 16 which is pBS9.

25. The cloning vector of claim 16 which is pBS10.

26. The cloning vector of claim 16 which is pBS49.

27. The cloning vector of claim 16 which is pBS60.

28. A transformed restrictionless host cell comprising a recombinant DNA cloning vector of claim 1 subject to the limitation that said host cell, prior to transformation, is sensitive to an antibiotic for which resistance is conferred by a DNA segment comprising said vector, and further that at least one origin of replication comprising said vector is functional in said host cell.

29. The transformed restrictionless host cell of claim 28 in which the recombinant DNA cloning vector is selected from the group of plasmids consisting of pBS1, pBS2, pBS3, pBS4, pBS5, pBS6, pBS7, pBS8, pBS9, pBS10, pBS11, pBS12, pBS13, pBS14, pBS15, pBS16, pBS17, pBS18, pBS19, pBS20, pBS21, pBS22, pBS23, pBS24, pBS25, pBS26, pBS27, pBS28, pBS29, pBS30, pBS31, pBS32, pBS33, pBS34, pBS35, pBS36, pBS37, pBS38, pBS39, pBS40, pBS41, pBS42, pBS43, pBS44, pBS45, pBS46, pBS47, pBS48, pBS49, pBS50, pBS51, pBS52, pBS53, pBS54, pBS55, pBS56, pBS57, pBS58, pBS59, and pBS60.

30. The transformed host cell of claim 28 which is a Streptosporangium.

31. The transformed host cell of claim 28 which is a Actinoplanes.

32. The transformed host cell of claim 28 which is a Nocardia.

33. The transformed host cell of claim 28 which is a Micromonospora.

34. The transformed host cell of claim 28 which is a Staphylococcus.

35. The transformed host cell of claim 28 or 29 which is a Streptomyces.

36. The transformed host cell of claim 28 or 29 which is a Bacillus.

37. The transformed host cell of claim 28 or 29 which is *E. coli*.

38. The transformed host cell of claim 29 which is *Streptomyces fradiae.*

39. The transformed host cell of claim 29 which is *Streptomyces coelicolor.*

40. The transformed host cell of claim 29 which is *Streptomyces ambofaciens*/pBS1.

41. The transformed host cell of claim 29 which is *Streptomyces ambofaciens*/pBS2.

42. The transformed host cell of claim 29 which is *Streptomyces ambofaciens*/pBS5.

43. The transformed host cell of claim 29 which is *Streptomyces ambofaciens*/pBS7.

44. The transformed host cell of claim 29 which is *Bacillus subtilis* MI112/pBS1.

45. The transformed host cell of claim 29 which is *Bacillus subtilis* MI112/pBS2.

46. The transformed host cell of claim 29 which is *Bacillus subtilis* MI112/pBS5.

47. The transformed host cell of claim 29 which is *Bacillus subtilis* MI112/pBS7.

48. The transformed host cell of claim 29 *E. coli* K12 HB101/pBS9.

49. The transformed host cell of claim 29 which is *Streptomyces ambofaciens*/pBS9.

50. The transformed host cell of claim 29 which is *Bacillus subtilis* MI112/pBS9.

51. A recombinant DNA cloning vector selected from the group of plasmids consisting of pHI-16 and pHI-18.

52. A *Bacillus subtilis* MI112 host cell that is transformed with a recombinant DNA cloning vector of claim 51.

* * * * *